US012586228B2

(12) United States Patent
Pak et al.

(10) Patent No.: US 12,586,228 B2
(45) Date of Patent: Mar. 24, 2026

(54) DEVICE AND METHOD FOR CALCULATING ATRIAL WALL THICKNESS

(71) Applicant: INDUSTRY-ACADEMIC COOPERATION FOUNDATION YONSEI UNIVERSITY, Seoul (KR)

(72) Inventors: Hui-Nam Pak, Seoul (KR); Oh Seok Kwon, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 267 days.

(21) Appl. No.: 18/518,563

(22) Filed: Nov. 23, 2023

(65) Prior Publication Data
US 2024/0087154 A1 Mar. 14, 2024

Related U.S. Application Data

(63) Continuation of application No. PCT/KR2022/007850, filed on Jun. 2, 2022.

(30) Foreign Application Priority Data

Jun. 3, 2021 (KR) ........................ 10-2021-0072245
Jun. 2, 2022 (KR) ........................ 10-2022-0067621

(51) Int. Cl.
G06T 7/62 (2017.01)
A61B 6/50 (2024.01)
(Continued)

(52) U.S. Cl.
CPC ................ G06T 7/62 (2017.01); A61B 6/503 (2013.01); G06T 7/0012 (2013.01); G16H 50/50 (2018.01);
(Continued)

(58) Field of Classification Search
CPC ..................... G06T 7/62; G06T 7/0012; G06T 2207/10081; G06T 2207/30048;
(Continued)

(56) References Cited

U.S. PATENT DOCUMENTS

2011/0319763 A1    12/2011   Subramanian et al.
2017/0004618 A1*   1/2017   Voigt ........................ G06T 7/62
2018/0259608 A1*   9/2018   Golden .................. G06N 3/084

FOREIGN PATENT DOCUMENTS

JP          2004267393         *   9/2004
JP          2004267393   A       9/2004
(Continued)

OTHER PUBLICATIONS

International search report of PCT/KR2022/007850, Sep. 6, 2022, English trasniation.

*Primary Examiner* — Siamak Harandi
(74) *Attorney, Agent, or Firm* — STIP Law Group, LLC

(57) ABSTRACT

A method of calculating an atrial wall thickness through a device including a processor and a memory according to an embodiment of the present disclosure may include (a) receiving image data for a patient's atrium as input data, (b) calculating endocardial and epicardial borders corresponding to starting and ending points of the atrial wall thickness from the received input data, and (c) calculating the patient's atrial wall thickness using the calculated endocardial and epicardial borders, wherein the image data for the patient's atrium received in the step (a) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than
(Continued)

Start

Extract one or more pixels corresponding to atrial wall region from received input data, and apply convex hull algorithm thereto to calculate three-dimensional atrial envelope for patient's atrium — S220-1

Set initial boundary condition for performing Poisson equation for calculated three-dimensional atrial envelope — S220-2

Repeatedly perform Poisson equation N times on three-dimensional atrial envelope based on set initial boundary condition, and calculate border of atrial wall region in three-dimensional atrial envelope and border of non-eroded region in open region — S220-3

Perform binarization on region corresponding to atrium and other regions based on calculated borders of the atrial wall region and non-eroded region in open region — S220-4

End the patient's heart, respectively, are assigned with labels having different numerals for the respective regions.

13 Claims, 26 Drawing Sheets

(51) Int. Cl.
   *G06T 7/00*       (2017.01)
   *G06T 7/136*     (2017.01)
   *G16H 50/50*    (2018.01)
(52) U.S. Cl.
   CPC .............. *G06T 2207/10081* (2013.01); *G06T 2207/30048* (2013.01)
(58) Field of Classification Search
   CPC ... G06T 7/12; G06T 7/136; G06T 7/11; G06T 7/187; A61B 6/503; A61B 6/5217; A61B 6/032; G16H 50/50; G16H 50/20
   See application file for complete search history.

(56)             References Cited

FOREIGN PATENT DOCUMENTS

| | | |
|---|---|---|
| JP | 2019504659 A | 2/2019 |
| KR | 20110077795 A | 7/2011 |
| KR | 20120050595 A | 5/2012 |
| KR | 20200095967 A | 8/2020 |

* cited by examiner

<u>100</u>

Start

Receive image data for patient's atrium as input data    S210

Calculate endocardial and epicardial borders corresponding to start and end points of atrial wall thickness from received input data    S220

Finally calculate patient's atrial wall thickness using calculated endocardial and epicardial borders    S230

End

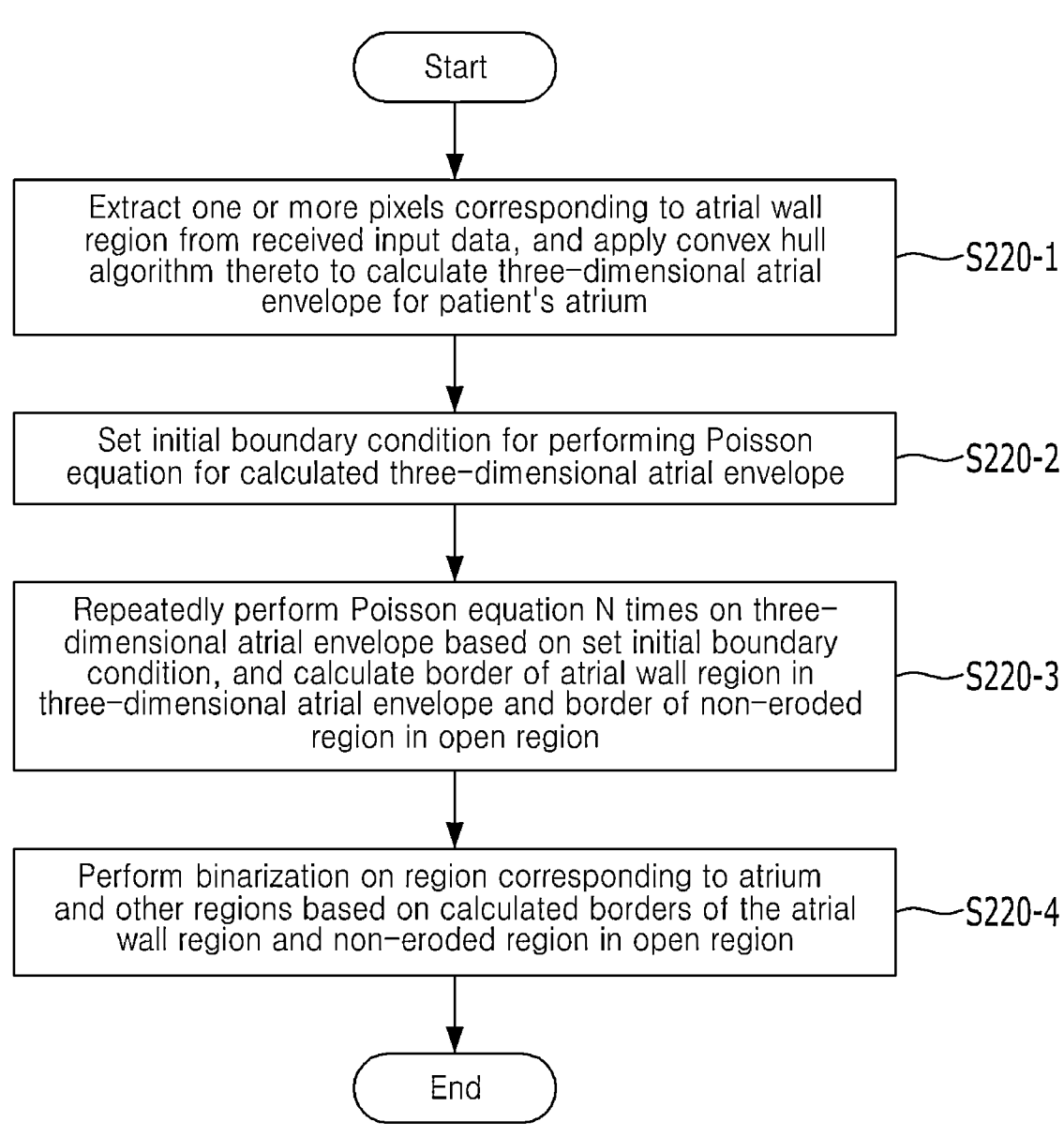

Start

Extract one or more pixels corresponding to atrial wall region from received input data, and apply convex hull algorithm thereto to calculate three-dimensional atrial envelope for patient's atrium — S220-1

Set initial boundary condition for performing Poisson equation for calculated three-dimensional atrial envelope — S220-2

Repeatedly perform Poisson equation N times on three-dimensional atrial envelope based on set initial boundary condition, and calculate border of atrial wall region in three-dimensional atrial envelope and border of non-eroded region in open region — S220-3

Perform binarization on region corresponding to atrium and other regions based on calculated borders of the atrial wall region and non-eroded region in open region — S220-4

End

Fig. 21

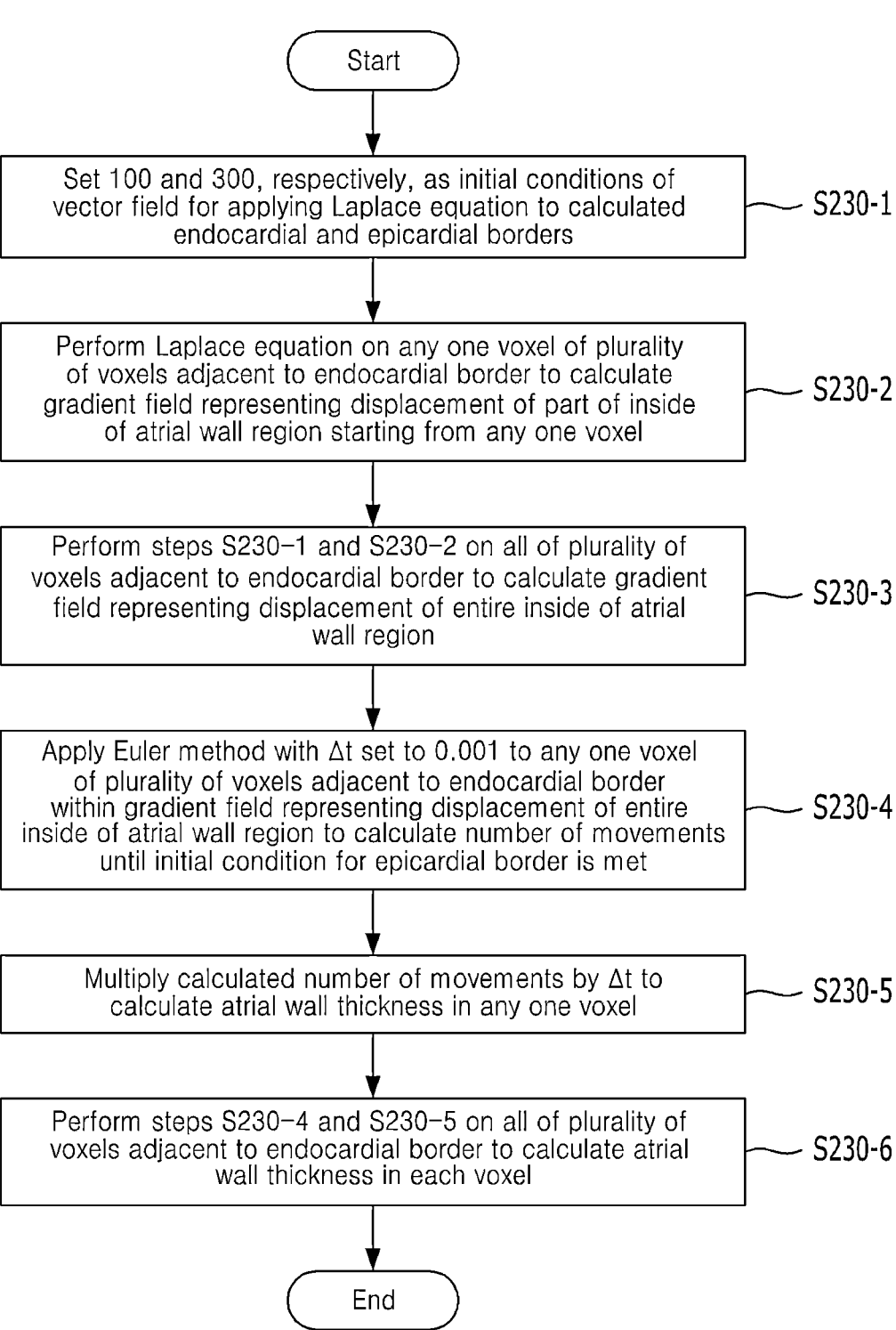

Start

Set 100 and 300, respectively, as initial conditions of vector field for applying Laplace equation to calculated endocardial and epicardial borders — S230-1

Perform Laplace equation on any one voxel of plurality of voxels adjacent to endocardial border to calculate gradient field representing displacement of part of inside of atrial wall region starting from any one voxel — S230-2

Perform steps S230-1 and S230-2 on all of plurality of voxels adjacent to endocardial border to calculate gradient field representing displacement of entire inside of atrial wall region — S230-3

Apply Euler method with Δt set to 0.001 to any one voxel of plurality of voxels adjacent to endocardial border within gradient field representing displacement of entire inside of atrial wall region to calculate number of movements until initial condition for epicardial border is met — S230-4

Multiply calculated number of movements by Δt to calculate atrial wall thickness in any one voxel — S230-5

Perform steps S230-4 and S230-5 on all of plurality of voxels adjacent to endocardial border to calculate atrial wall thickness in each voxel — S230-6

End

DEVICE AND METHOD FOR CALCULATING ATRIAL WALL THICKNESS

CROSS-REFERENCE TO RELATED APPLICATIONS

This application is a Continuation of Application No. PCT/KR2022/007850, filed on Jun. 2, 2022, which in turn claims the benefit of Korean Patent Applications No. 10-2021-0072245, filed on Jun. 3, 2021, and No. 10-2022-0067621, filed on Jun. 2, 2022. The entire disclosures of all these applications are hereby incorporated by reference.

TECHNICAL FIELD

The present disclosure relates to a device and method of calculating an atrial wall thickness. More specifically, the present disclosure relates to a device and method that is applicable to commercially available atrial wall automatic segmentation software and does not require manual work based on a clinician's experience.

BACKGROUND ART

Arrhythmia refers to a symptom in which the heartbeat becomes abnormally fast, slow, or irregular since the heart is unable to produce electrical impulses or the impulses are not transmitted properly due to a failure of regular contractions to continue, and atrial fibrillation is a main cause, which in severe cases, may lead to a sudden death or stroke.

Treatment methods for such an arrhythmia include a surgical treatment that blocks electrical conduction of the heart by cauterizing heart tissue, such as a high-frequency electrode catheter ablation procedure, to prevent the arrhythmia, but there is a problem in that it is difficult to determine in advance which part of the heart and at what intensity the ablation procedure should be performed to derive an optimal effect.

However, the problem of the high-frequency electrode catheter ablation procedure may be easily solved when a thickness of the heart can be accurately measured in real time, which is because the optimal effect can be derived by a customized ablation procedure through performing the ablation procedure with a low intensity on an area measured as having a low thickness, and performing the ablation procedure with a high intensity on an area measured as having a high thickness, and accordingly, studies on methods of measuring heart thickness through various means have been actively carried out.

In connection therewith, the applicant disclosed a technology of measuring an atrial wall thickness from computed tomography (CT) scans in Publication No. 10-2020-0095967 (hereinafter referred to as 'prior art'), but was proposed while being strongly coupled to a customized atrial wall segmentation technology, and thus has a problem that is not applicable to recently commercialized atrial wall automatic segmentation software, and cannot be considered a fully automated technology because a clinician must manually specify the endocardium and epicardium corresponding to starting and ending points of the atrial wall, and has a problem in that deviations in atrial wall measurement results may occur depending on the clinician's experience.

The present disclosure relates to a new and groundbreaking technology that solves those problems of the prior art so as to be applicable to commercially available atrial wall automatic segmentation software while at the same time no manual operation is required based on the clinician's experience.

DISCLOSURE OF INVENTION

Technical Problem

A technical problem to be solved by the present disclosure is to provide a device and method of calculating an atrial wall thickness that is applicable to commercially available automatic atrial wall segmentation software.

Another technical problem to be solved by the present disclosure is to provide a device and method of calculating an atrial wall thickness so as to fully automatically define the endocardium and epicardium corresponding to starting and ending points of the atrial wall, without manually specifying them according to the clinician's experience.

Technical problems of the present disclosure are not limited to the above-mentioned problems, and other technical problems which are not mentioned herein will be clearly understood by those skilled in the art from the description below.

Technical Solution

In order to solve the foregoing technical problems, a method of calculating an atrial wall thickness through a device including a processor and a memory according to an embodiment of the present disclosure may include (a) receiving image data for a patient's atrium as input data, (b) calculating endocardial and epicardial borders corresponding to starting and ending points of the atrial wall thickness from the received input data, and (c) calculating the patient's atrial wall thickness using the calculated endocardial and epicardial borders, wherein the image data for the patient's atrium received in the step (a) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than the patient's heart, respectively, are assigned with labels having different numerals for the respective regions.

According to one embodiment, the step (b) may include at least one of: (b-1) extracting one or more pixels corresponding to an atrial wall region from the received input data, and applying a convex hull algorithm thereto to calculate a three-dimensional atrial envelope for the patient's atrium, (b-2) setting an initial boundary condition for performing a Poisson equation on the calculated three-dimensional atrial envelope, (b-3) repeatedly performing the Poisson equation N times (N is a natural number) on the three-dimensional atrial envelope, and calculating a border of an atrial wall region in the three-dimensional atrial envelope and a border of a non-eroded region in an open region, and (b-4) performing binarization for a region corresponding to the atrium and a region other than the atrium based on the calculated borders of the atrial wall region and the non-eroded region in the open region.

According to one embodiment, the step (b-1) may include at least one of: (b-1-1) extracting one or more pixels for the atrial wall region from any one of a plurality of mask label image data for each tomography image of the patient's atrium, which is the received input data, (b-1-2) calculating a two-dimensional atrial envelope including an entire atrial wall region from which the one or more pixels are extracted thereinside by applying a convex hull algorithm thereto, (b-1-3) performing the steps (b-1-1) and (b-1-2) for all of the plurality of mask label image data to calculate a plurality of two-dimensional atrial envelopes corresponding to the plurality of mask label image data, respectively, and (b-1-4) merging the calculated plurality of two-dimensional atrial envelopes to calculate a three-dimensional atrial envelope for the patient's atrium.

According to one embodiment, the initial boundary condition set in the step (b-2) may be a Neumann boundary condition for the atrial wall region included in the calculated three-dimensional atrial envelope, and a Dirichlet boundary condition for a region other than the calculated three-dimensional atrial envelope.

According to one embodiment, the Poisson equation performed in the step (b-3) may be performed through a Jacobi iteration method, and in this case, the number N may be 100.

According to one embodiment, a border of the atrial wall region and a border of the non-eroded region in the open region, which are included in the three-dimensional atrial envelope, may be calculated by applying a cutoff frequency of 0.1 thereto.

According to one embodiment, the method may further include: subsequent to the step (b-4), (b-5) removing residues using a border of the region corresponding to the atrium in which binarization has been performed and one or more pixels corresponding to the atrial wall region.

According to one embodiment, the step (b-5) may include at least one of: (b-5-1) removing one or more pixels corresponding to the extracted atrial wall region from the border of the region corresponding to the atrium in which binarization has been performed; (b-5-2) applying a connected component label algorithm to a region corresponding to the atrium from which one or more pixels corresponding to the atrial wall region have been removed to assign labels to an interconnected region in the region corresponding to the atrium; and (b-5-3) measuring a volume of each label for the interconnected region assigned with the labels, and removing the remaining region except for a region with the largest volume as residues.

According to one embodiment, the method may further include: subsequent to the step (b-5), (b-6) applying a 3D connection filter to each voxel corresponding to the atrial wall region including the region corresponding to the atrium to determine whether the voxel corresponds to any one region of the endocardium, myocardium, and epicardium, and labeling it to calculate endocardial and epicardial borders.

According to one embodiment, as a result of applying a 3D connection filter to each voxel, the region may be determined as the epicardium when more than half of voxels adjacent thereto are voxels for a region other than the region corresponding to the atrium, as the myocardium when more than half of voxels adjacent thereto are voxels for the atrial wall region, and as the endocardium when more than half of voxels adjacent thereto are voxels for a region having the largest volume.

According to one embodiment, the step (c) may include at least one of: (c-1) setting 100 and 300 as initial conditions of a vector field for applying a Laplace equation to the calculated endocardial and epicardial borders, respectively, (c-2) performing the Laplace equation on any one voxel of a plurality of voxels adjacent to the endocardial border to calculate a gradient field representing a displacement of a part of an inside of the atrial wall region starting from the any one voxel, (c-3) performing the steps (c-1) and (c-2) on all of the plurality of voxels adjacent to the endocardial border to calculate a gradient field representing a displacement of an entire inside of the atrial wall region, (c-4) applying an Euler method with $\Delta t$ set to 0.001 to any one voxel of a plurality of voxels adjacent to the endocardial border within the calculated gradient field representing the displacement of the entire inside of the atrial wall region to calculate a number of movements until an initial condition for the epicardial border is met, (c-5) multiplying the calculated number of movements by $\Delta t$ to calculate an atrial wall thickness in the any one voxel, and (c-6) performing the steps (c-4) and (c-5) on all of the plurality of voxels adjacent to the endocardial border to calculate an atrial wall thickness in each voxel.

According to one embodiment, the Laplace equation performed in the step (c-2) may be performed through a Jacobi iteration method, and as for a stopping condition, a stopping condition equation Ei as shown below may be 10-5, or a number of repetitions may be 400 or more. Stopping condition equation $E_i = \Sigma[(\Delta\Psi_i/\Delta x)^2 + (\Delta\Psi_i/\Delta y)^2(\Delta\Psi_i/\Delta z)^2]^{1/2}$ In order to solve the foregoing technical problems, a device of calculating an atrial wall thickness according to another embodiment of the present disclosure may include one or more processors, a network interface, a memory that loads a computer program executed by the processor, and a storage that stores large-capacity network data and the computer program, wherein the computer program includes, by the one or more processors, (A) an operation of receiving image data for a patient's atrium as input data, (B) an operation of calculating endocardial and epicardial borders corresponding to starting and ending points of the atrial wall thickness from the received input data, and (C) an operation of calculating the patient's atrial wall thickness using the calculated boundaries of the endocardium and epicardium, and the image data for the patient's atrium received in the operation (A) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions.

In order to solve the foregoing technical problems, a computer program stored on a medium according to still another embodiment of the present disclosure may include (AA) receiving, in connection with a computing device, image data for the patient's atrium as input data, (BB) calculating endocardial and epicardial borders corresponding to starting and ending points of the atrial wall thickness from the received input data, and (CC) calculating the patient's atrial wall thickness using the calculated boundaries of the endocardium and epicardium, wherein the image data for the patient's atrium received in the step (AA) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions.

Advantageous Effects

According to the present disclosure as described above, mask label image data, which is input data used to calculate a patient's atrial wall thickness, may be generated by commercially available atrial wall automatic segmentation software to be received therefrom and thus may not be strongly coupled to a customized atrial wall segmentation technology as in the prior art, thereby having an effect of being easily applicable to and having high compatibility with commercially available atrial wall automatic segmentation software.

Furthermore, simply by receiving the input data, the patient's atrial wall thickness may be calculated fully automatically without receiving any input from a clinician, thereby having an effect of acquiring consistent atrial wall thickness calculation results.

Furthermore, when a processor is implemented as a processor capable of parallel processing, the patient's atrial wall thickness may be calculated and output in real time, thereby having an effect of facilitating the determination of a surgical intensity of a high-frequency electrode catheter ablation procedure.

The effects of the present disclosure are not limited to the above-mentioned effects, and other effects that are not mentioned herein will be clearly understood by those skilled in the art from the description below.

BRIEF DESCRIPTION OF THE DRAWINGS

Figure 3:
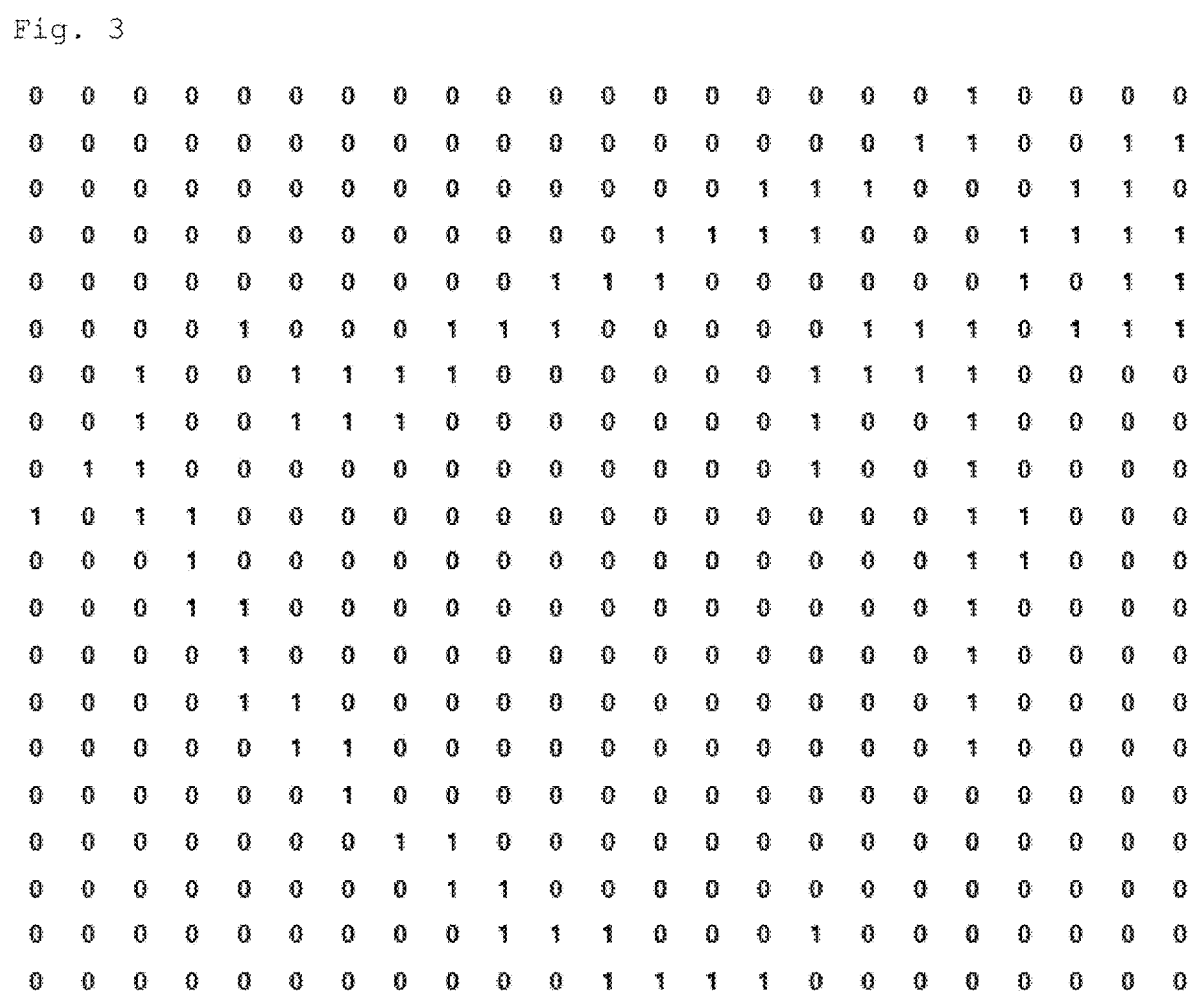

FIG. 3 is a diagram illustratively showing mask label image data.

FIG. 4 is a diagram illustratively showing a view of mask label image data overlaid on a CT scan.

FIG. 6 is a flowchart illustrating a step S220 of calculating endocardial and epicardial borders in the method of calculating an atrial wall thickness according to the second embodiment of the present disclosure.

FIG. 21 is a flowchart illustrating a step S230 of calculating an atrial wall thickness in the method of calculating the atrial wall thickness according to the second embodiment of the present disclosure.

FIG. 25 is a diagram illustratively showing a view in which a patient's atrium is divided into zones.

BEST MODE FOR CARRYING OUT THE INVENTION

Figure 1:
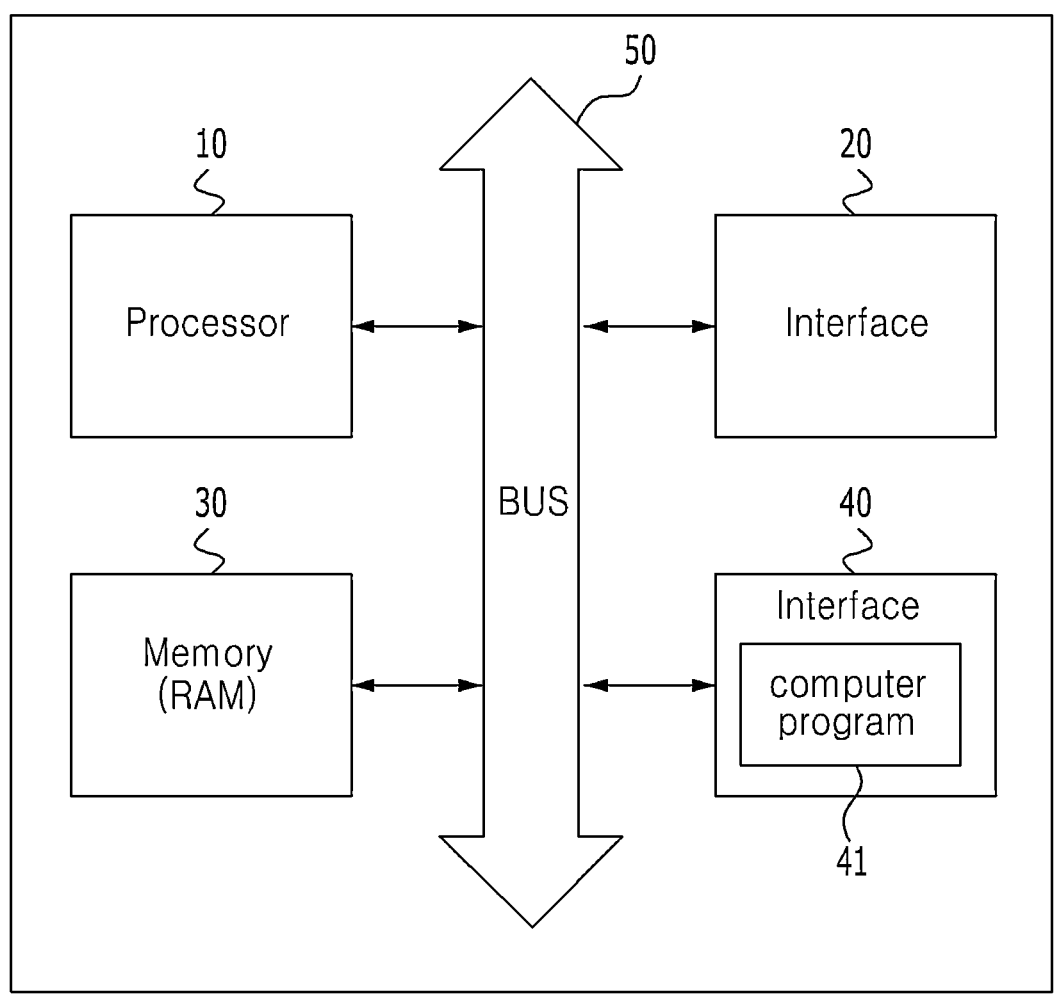
FIG. 1 is a diagram showing an overall configuration included in a device of calculating an atrial wall thickness according to a first embodiment of the present disclosure.

Hereinafter, preferred embodiments of the present disclosure will be described in detail with reference to the accompanying drawings. Advantages and features of the present disclosure, and methods of accomplishing the same will be clearly understood with reference to the following embodiments described in detail in conjunction with the accompanying drawings. However, the present disclosure is not limited to those embodiments disclosed below but may be implemented in various different forms. It should be noted that the present embodiments are merely provided to make a full disclosure of the invention and also to allow those skilled in the art to know the full range of the invention, and therefore, the present disclosure is to be defined only by the scope of the appended claims. Further, like reference numerals refer to like or similar elements throughout the specification.

Unless otherwise defined, all terms (including technical and scientific terms) used in this specification may be used with meanings that can be commonly understood by those skilled in the art to which the present disclosure pertains.

Additionally, terms defined in commonly used dictionaries are not interpreted ideally or excessively unless clearly specifically defined.

It should be noted that the terms used herein are merely used to describe the embodiments, but not to limit the present disclosure. In this specification, unless clearly used otherwise, expressions in a singular form include a plural form.

The term "comprises" and/or "comprising" used in the specification intend to express a constituent element, a step, an operation and/or a device does not exclude the existence or addition of one or more other constituent elements, steps, operations and/or devices.

FIG. 1 is a diagram showing an overall configuration included in a device 100 of calculating an atrial wall thickness according to a first embodiment of the present disclosure.

However, this is only a preferred embodiment for achieving the objectives of the present disclosure, and some components may be added thereto or deleted therefrom as needed, and a function performed by any one component may, of course, be performed together with other components.

The device 100 of calculating an atrial wall thickness according to a first embodiment of the present disclosure may include a processor 10, a network interface 20, a memory 30, a storage 40, and a data bus 50 connecting them to one another.

The processor 10 controls an overall operation of each component. The processor 10 may be any one of a central processing unit (CPU), a microprocessor unit (MPU), a micro controller unit (MCU), or a type of processor widely known in the art to which the present disclosure pertains. Moreover, the processor 10 may perform calculations on at least one application or program for performing a method of calculating an atrial wall thickness according to a second embodiment of the present disclosure, and may be preferably implemented as a parallel type artificial intelligence processor.

The network interface 20 may support wired and wireless Internet communication of the device 100 of calculating an atrial wall thickness according to the first embodiment of the present disclosure, and may also support other known communication methods. Therefore, the network interface 20 may include a communication module according thereto.

The memory 30 may store various types of data, commands, and/or information, and load one or more computer programs 41 from the storage 40 in order to perform a method of calculating an atrial wall thickness according to the second embodiment of the present disclosure. Although a RAM is shown as a type of the memory 30 in FIG. 1, various storage media may, of course, be used for the memory 30 in addition thereto.

The storage 40 may non-temporarily store one or more computer programs 41 and mass network data 42. The storage 40 may be any one of a non-volatile memory such as a read only memory (ROM), an erasable programmable ROM (EPROM), an electrically erasable programmable ROM (EEPROM), a flash memory, or the like, a hard disk, a removable disk, and a type of computer-readable recording medium widely known in the art to which the present disclosure pertains.

The computer program 41 may be loaded by the memory 30 to include, by the one or more processors, (A) an operation of receiving image data for a patient's atrium as input data, (B) an operation of calculating endocardial and epicardial borders corresponding to starting and ending points of the atrial wall thickness from the received input data, and (C) an operation of calculating the patient's atrial wall thickness using the calculated boundaries of the endocardium and epicardium, wherein the image data for the patient's atrium received in the operation (A) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions.

The operations performed by the computer program 41 briefly mentioned up to the present may be regarded as one function of the computer program 41, and a more detailed description will be described later in the description of a method of calculating an atrial wall thickness according to the second embodiment of the present disclosure.

The data bus 50 serves as a transfer path for commands and/or information among the processor 10, the network interface 20, the memory 30, and the storage 40 described above.

The device 100 of calculating an atrial wall thickness according to the first embodiment of the present disclosure described above may be a physically independent electronic device, but may be required to receive image data about a patient's atrium from a server (not shown) operated by a medical institution such as a hospital or a server (not shown) operated by a professional organization that specializes in handling medical data, and the like, and in this case, may also be implemented as a function of the server, and in this case, the server may of course be a tangible physical server or a virtual cloud server.

Hereinafter, the method of calculating an atrial wall thickness according to the second embodiment of the present disclosure will be described with reference to FIGS. 2 to 26.

Figure 2:
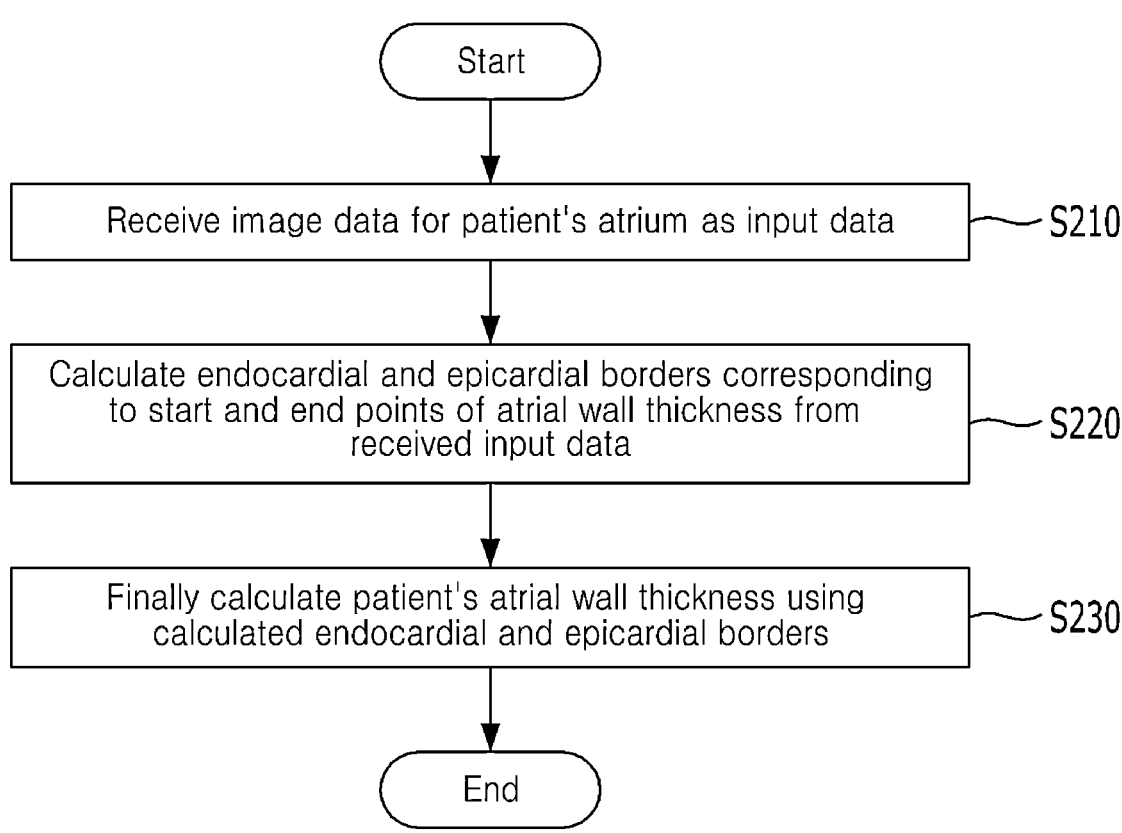
FIG. 2 is a flowchart showing representative steps in a method of calculating an atrial wall thickness according to a second embodiment of the present disclosure.

FIG. 2 is a flowchart showing representative steps in a method of calculating an atrial wall thickness according to a second embodiment of the present disclosure.

This is only a preferred embodiment in achieving the objectives of the present disclosure, and some steps may be added thereto or deleted therefrom as needed, and furthermore, any one step may of course be included in another step.

Meanwhile, all steps are assumed to be performed by the device 100 of calculating an atrial wall thickness according to the first embodiment of the present disclosure, and hereinafter, will be simply referred to as the device 100 including a processor and a memory.

First, the device 100 including a processor and a memory receives image data for a patient's atrium as input data (S210).

Here, the image data for the patient's atrium received as input data is a plurality of mask label image data for each tomographic image of the patient's atrium acquired from a computed tomography (CT) scans of the patient's atrium, and this mask label image data may be generated by commercially available atrial wall automatic segmentation software to be received therefrom, and when the device 100 including a processor and a memory is implemented to include the atrial wall automatic segmentation software or to perform functions corresponding thereto, receiving herein may refer to loading.

Figure 4:
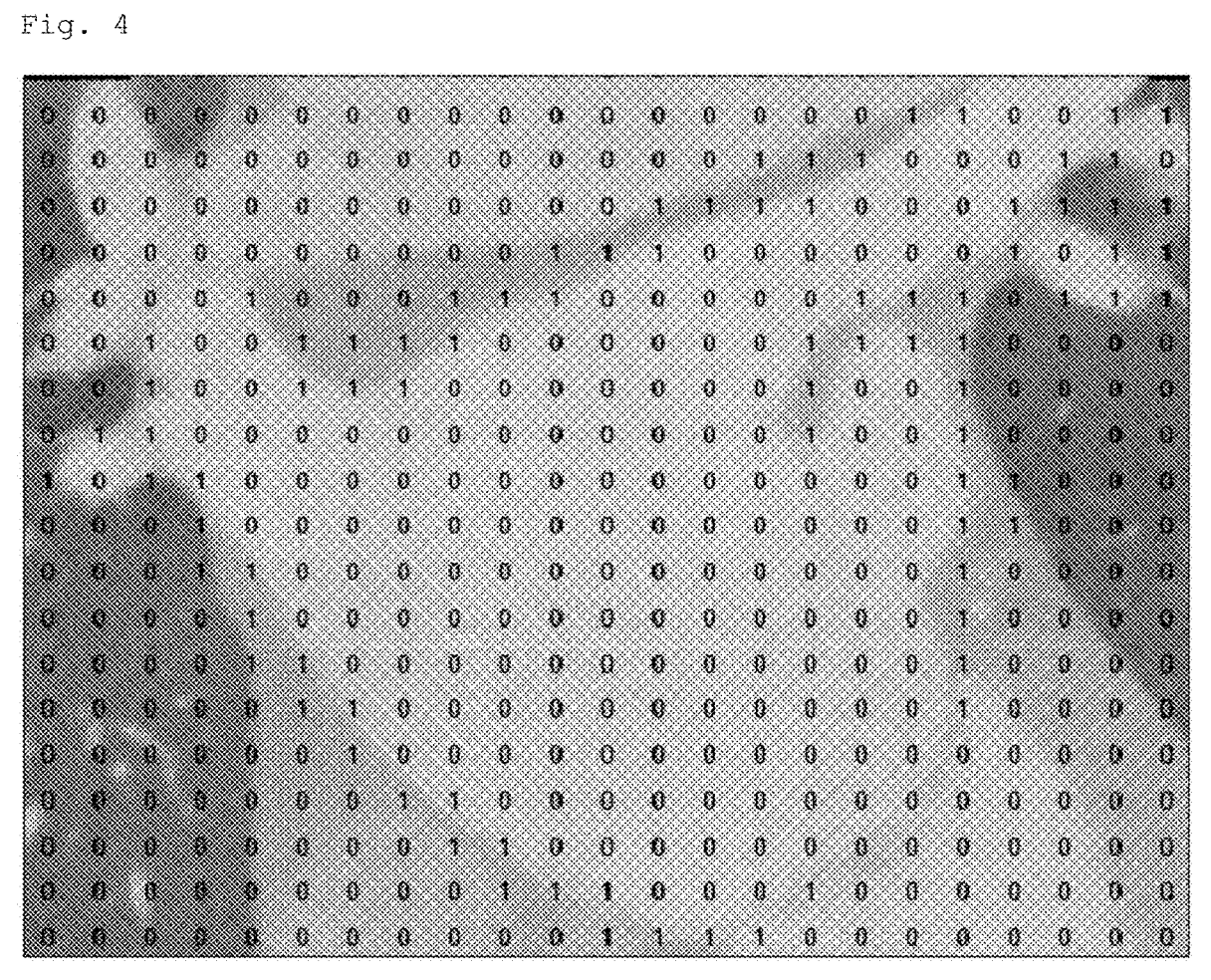

More specifically, the mask label image data may be data in which one or more pixels corresponding to an atrial wall region including the patient's atrium and an inside region of the atrium, other regions within the patient's heart disposed around the patient's atrium, and regions other than the patient's heart, respectively, are assigned with labels having different numerals for the respective regions Separately, when receiving a plurality of mask label image data, the device 100 including a processor and a memory may receive each CT scan corresponding thereto, which is to adjust the unit of thickness and 3D coordinates, for example, millimeters (mm), but even when the CT scan is not received together, only tag information on the measurement unit may be received separately, and a view of mask label image data overlaid on a CT scan is illustratively shown in FIG. 4.

Meanwhile, there are a plurality of mask label image data, which are the input data to be received, since the CT scan of the patient's heart itself is a three-dimensional structure, and imaging may be carried out on the patient's heart on a plurality of cross-sections from the bottom end portion to the top end portion, and accordingly, the number of mask label image data received may correspond one-to-one to the number of tomographic images of the patient's atrium.

When image data for the patient's atrium is received as input data, the device 100 including a processor and a memory calculates endocardial and epicardial borders corresponding to start and end points of an atrial wall thickness from the received input data (S220).

Figure 5:
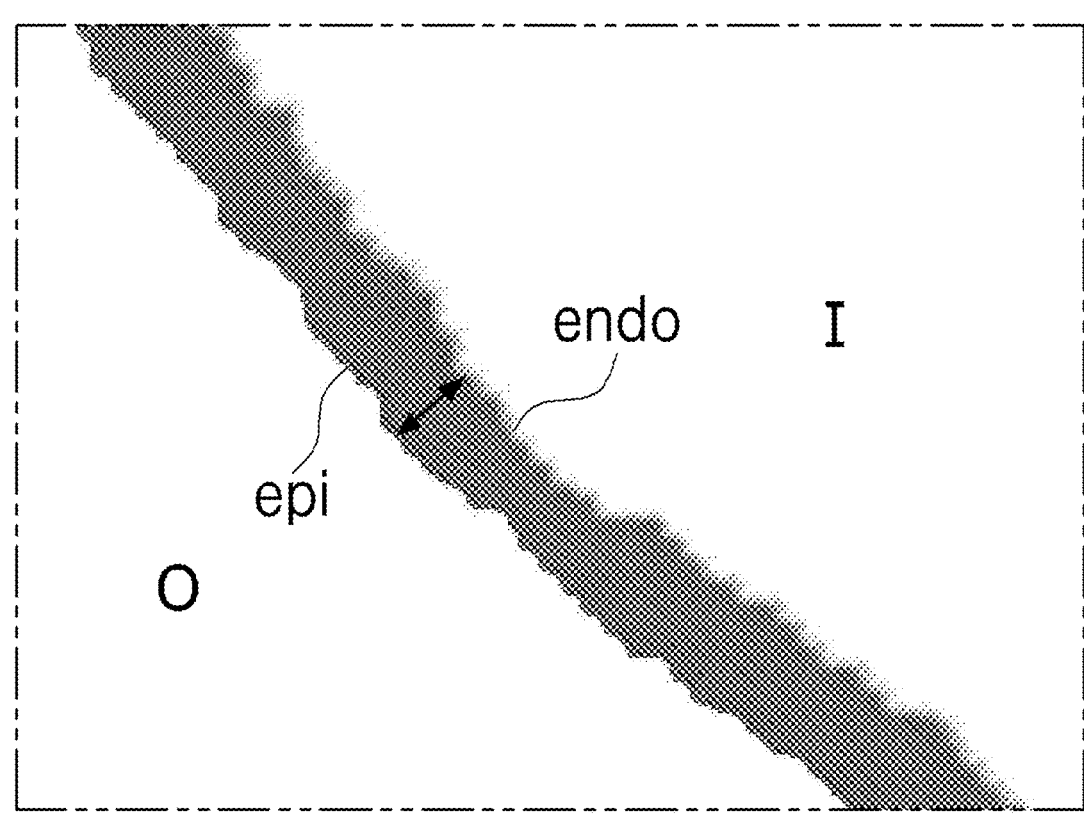
FIG. 5 is a diagram illustratively showing a cross-section of a patient's heart, which is a three-dimensional structure.

Here, with reference to FIG. 5, in which it is illustratively shown an enlarged portion of a cross-section of a patient's heart that is a three-dimensional structure with regard to endocardial and epicardial borders corresponding to starting and ending points of the atrial wall thickness, an inner region (I) and an outer region (O) of the atrium may be distinguished due to the atrial wall, and part of the atrial wall in contact with the inner region (I) of the atrium is the endocardium (endo), and part of the atrium in contact with the outer region (O) of the atrium is the epicardium (epi), and thus it can be easily seen that the atrial wall thickness is a distance (arrow) from the starting point, which is the endocardium, to the ending point, which is the epicardium.

Therefore, accurately calculating endocardial and epicardial borders has a very important technical significance in the method of calculating an atrial wall thickness according to the second embodiment of the present disclosure, which will be described in detail with reference to FIG. 6 below.

FIG. 6 is a flowchart illustrating a step S220 of calculating endocardial and epicardial borders in the method of calculating an atrial wall thickness according to the second embodiment of the present disclosure.

This is only a preferred embodiment in achieving the objectives of the present disclosure, and some steps may be added thereto or deleted therefrom as needed, and furthermore, any one step may of course be included in another step.

Prior to detailed description thereof, the concept employed to calculate endocardial and epicardial borders represents the phenomenon of maintaining a temperature difference between the outside and the inside, like the heat preservation mechanism of an igloo because the heart itself has a geometrically open structure, wherein the heart being "open" denotes a portion whose cross-section cannot be expressed as the atrial wall, as shown above in FIG. 5, or an entrance portion when substituted into an igloo, which can be said to be a region where the atrium and other structures such as arteries or veins are connected, and the word "open" is used because it cannot be expressed as an atrial wall.

First, the device 100 including a processor and a memory extracts one or more pixels corresponding to an atrial wall region from the received input data, and applies a convex hull algorithm thereto to calculate a three-dimensional atrial envelope for the patient's atrium (S220-1).

Here, the convex hull algorithm is a known algorithm for finding vertices constituting a convex hull including all vertices from a given vertex, which may be applied to a plurality of mask label image data, that is, input data, to calculate a three-dimensional atrial hull for the patient's atrium, and the reason for calculating a three-dimensional atrial envelope will be described later in step S220-3.

Figure 7:
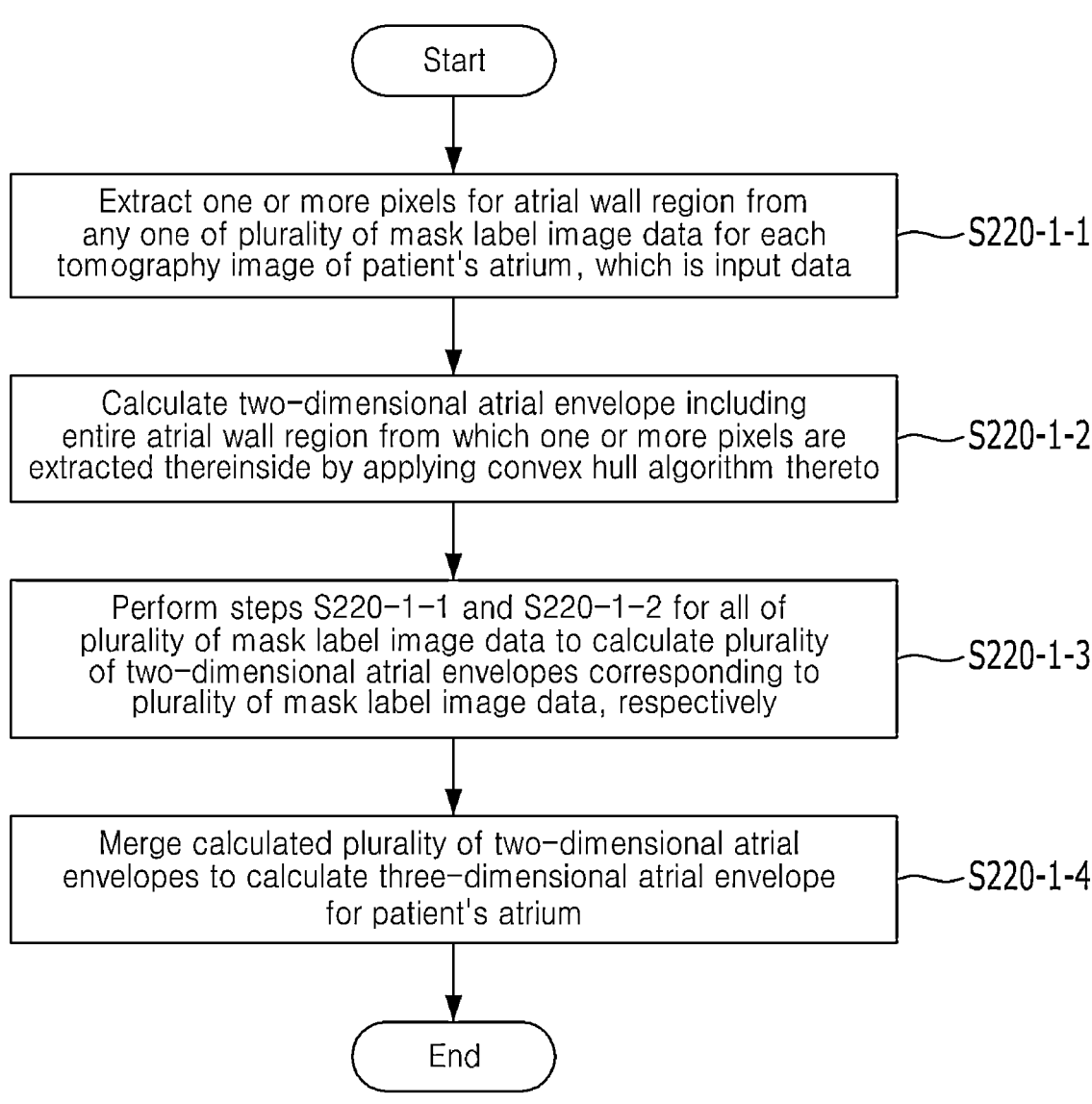
FIG. 7 is a flowchart illustrating a step S220-1 of calculating a three-dimensional atrial envelope.

Referring to FIG. 7, which is a flowchart of a specific method of calculating a three-dimensional atrial envelope, step S220-1 may further include at least one of: extracting, by the device 100 including a processor and a memory, one or more pixels for an atrial wall region from any one of a plurality of mask label image data for each tomography image of the patient's atrium, which is input data (S220-1-1), calculating a two-dimensional atrial envelope including an entire atrial wall region from which the one or more pixels are extracted thereinside by applying a convex hull algorithm thereto (S220-1-2), performing the steps (S220-1-1) and (S220-1-2) for all of the plurality of mask label image data to calculate a plurality of two-dimensional atrial envelopes corresponding to the plurality of mask label image data, respectively (S220-1-3), and merging the calculated plurality of two-dimensional atrial envelopes to calculate a three-dimensional atrial envelope for the patient's atrium (S220-1-4).

Figure 8:
FIG. 8 is a diagram illustratively showing a view in which pixels assigned with a label having a numeral corresponding to an atrial wall region from mask label image data are extracted and visualized.

Describing each step in more detail, step S220-1-1 is to extract pixels assigned with a label having a numeral corresponding to an atrial wall region from any one of a plurality of mask label image data, which is visualized and illustratively shown in FIG. 8.

Meanwhile, any one of a plurality of mask label image data is sufficient as the mask label image data for extracting one or more pixels in step S220-1-1 as described above, but in order to improve the convenience of merging in calculating a three-dimensional atrial envelope in step S220-1-4, which will be described later, from among tomographic images of the patient's atrium, either one of mask label image data related to a tomographic image taken from a cross-section of the bottom end portion and mask label image data related to a tomographic image taken from a cross-section of the top end portion may be preferably used, but may not be necessarily limited to thereto.

Figure 9:
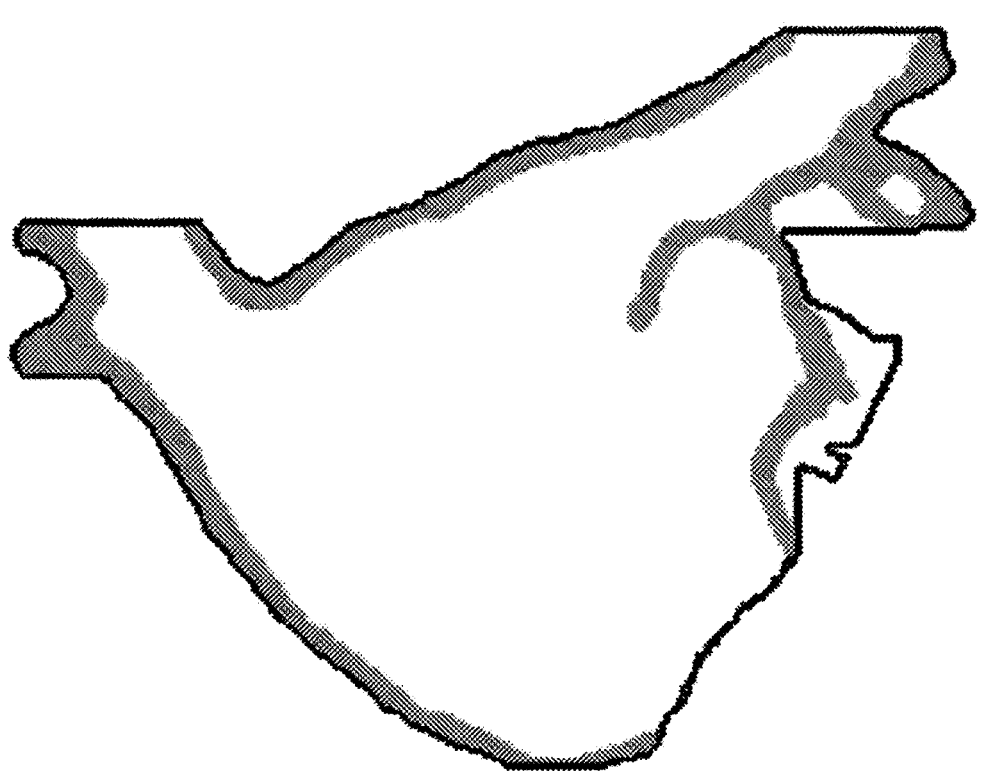
FIG. 9 is a diagram illustratively showing a two-dimensional atrial envelope.
Figure 10:
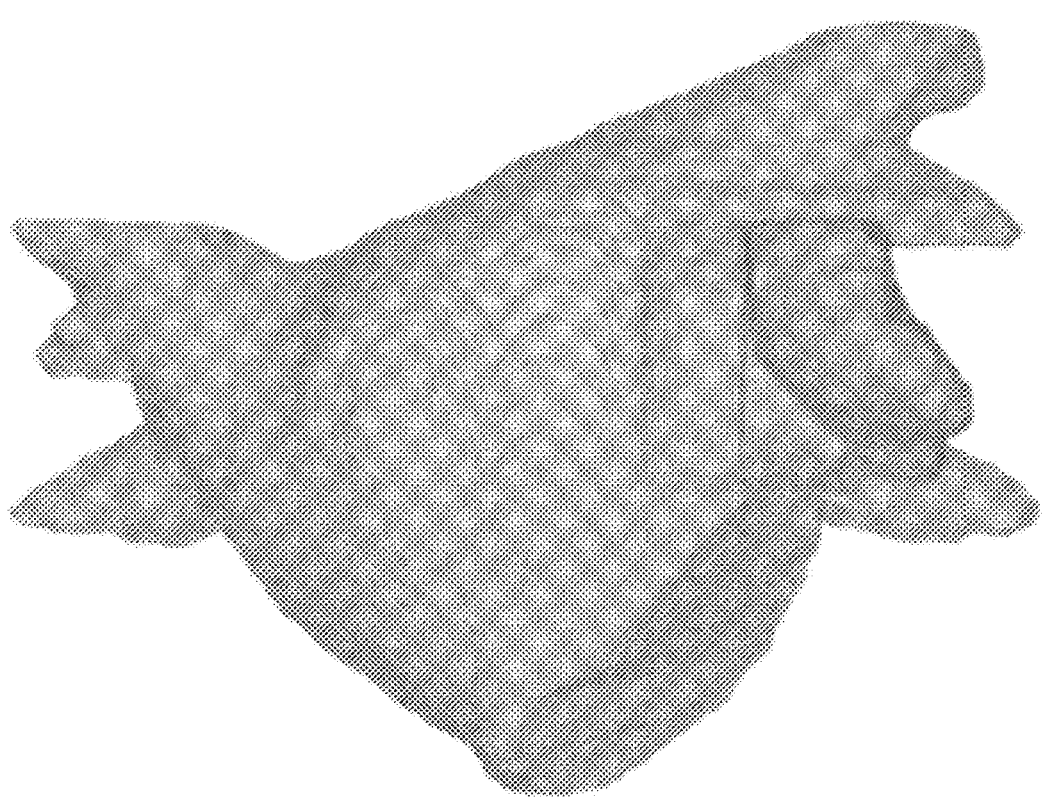
FIG. 10 is a diagram illustratively showing a two-dimensional atrial envelope.

In step S220-1-2, a two-dimensional atrial envelope including an entire atrial wall region calculated in step S220-1-1 is calculated, but a detailed description thereof will be omitted since a convex hull algorithm, which is a known algorithm, is applied thereto, and is visualized and illustratively shown in FIG. 9.

Referring to FIG. 9, it can be seen that thick lines, which are pixels corresponding to the atrial wall region shown in FIG. 8, are all included within a thin line corresponding to an atrial envelope, and it can be seen that an open region, which is a portion that cannot be expressed as an atrial wall, is also shown, and such an atrial envelope is calculated to perform a Poisson equation in the open region in step S220-3, which will be described later.

In step S220-1-3, steps S220-1-1 and S220-1-2 described above may be repeatedly performed for all of a plurality of mask label image data, and when performed on one mask label image data at a time, it would be preferable to improve the convenience of merging by performing the process on the mask label image data immediately following the mask label image data from which a two-dimensional atrial envelope has been calculated immediately before, but the present disclosure may not be necessarily limited thereto, and when implemented with a processor 10 capable of parallel processing, it will be performed on multiple mask label image data at the same time, and thus the computing speed may be improved, and accordingly, a three-dimensional atrial envelope calculation speed, which will be described later, may also be improved.

In step S220-1-4, a three-dimensional atrial envelope for the patient's atrium may be calculated by merging a two-dimensional atrial envelope for all mask label image data that have been calculated previously, and merging herein may be regarded as generating a three-dimensional atrial envelope through connecting two-dimensional atrial envelopes that have been calculated for respective cross-sections between that at the bottom end portion of the atrium to that at the top end portion thereof.

In this case, no matter how many two-dimensional atrial envelopes there are for each cross-section, it is difficult to represent them as a three-dimensional atrial envelope through merely connecting them as they are, because it can be seen that countless cross-sections are included between one cross-section and another cross-section. Accordingly, an atrial envelope between cross-sections may be calculated by applying an interpolation method or the like to one two-dimensional atrial envelope and the next two-dimensional atrial envelope, and optimized through separate calculations for redundant or overlapping regions, thereby calculating a three-dimensional atrial envelope including all pixels corresponding to the atrial wall region, and more specifically, three-dimensional atrial label pixels formed therefrom, as illustratively shown in FIG. 10.

The description of FIG. 6 will be provided again.

When the three-dimensional atrial envelope for the patient's atrium has been calculated, an initial boundary condition for performing a Poisson equation is set for the three-dimensional atrial envelope calculated by the device 100 including a processor and a memory (S220-2).

Here, a region where the Poisson equation, and more specifically a Poisson partial differential equation, is performed may be an inner region of the atrium, and may be performed on the three-dimensional atrial envelope described above in step S220-1, and the set initial boundary condition may be a Neumann boundary condition for an atrial wall region included in the three-dimensional atrial envelope, and a Dirichlet boundary condition for a region other than the three-dimensional atrial envelope.

Figure 11:
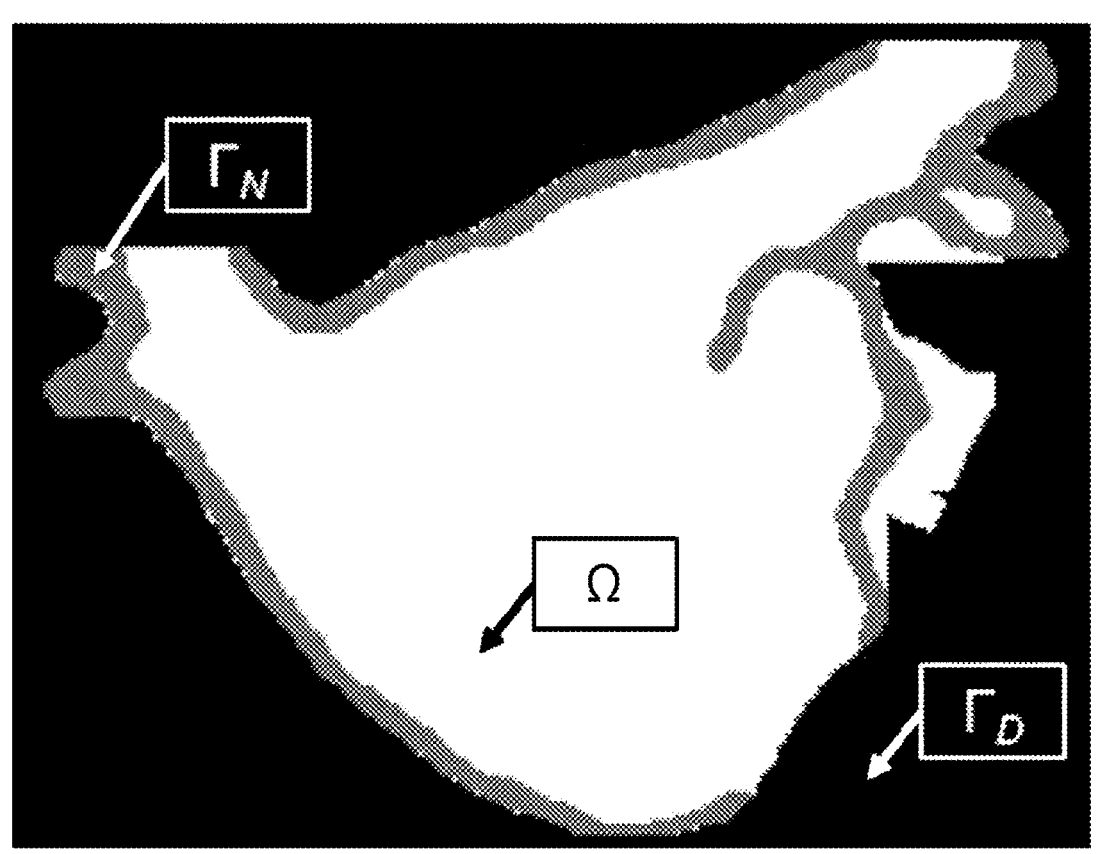
FIG. 11 is a diagram showing an inner region of the atrium that performs a Poisson equation on the two-dimensional atrial envelope shown in FIG. 9 and initial boundary conditions together.

In FIG. 11, for convenience of description, an inner region of the atrium where the Poisson equation is performed on the two-dimensional atrial envelope shown in FIG. 9, which corresponds to any one cross-section of the three-dimensional atrial envelope, is shown as $\Omega$ ($-\Delta u = f$ in $\Omega$), and it can be seen that a region other than the atrial envelope is set to a Dirichlet boundary condition ($\tau_D$, u=10 on $\tau_D$), and an atrial wall region is set to a Neumann boundary condition ($\tau_N$, $\delta u/\delta v = 0$ on $\tau_N$).

The description of FIG. 6 will be provided again.

When initial boundary conditions are set, the device 100 including a processor and a memory repeatedly performs the Poisson equation N times (N is a natural number) on the three-dimensional atrial envelope based on the set initial boundary conditions, and calculates a border of an atrial wall region in the three-dimensional atrial envelope and a border of a non-eroded region in an open region (S220-3).

Since the Poisson equation is performed on the three-dimensional atrial envelope based on the initial boundary conditions previously set in step S220-3, a rate of change may be calculated for an inner region ($\Omega$) of the atrium, the atrial wall region may not change according to the Neumann boundary condition, a region other than the atrial envelope may be distinguished from the inner region of the atrium and the atrial wall region according to the Dirichlet boundary condition, but may be calculated as a constant shape in which the rate of change itself does not exist.

Meanwhile, the Poisson equation herein may be performed through a Jacobi iteration method, and in this case, N, the number of iterations, may be 100, but may not be necessarily limited thereto, and an administrator or user of the device 100 including a processor and a memory may perform the Poisson equation through a different repetition method and setting the number of repetitions.

Figure 12:
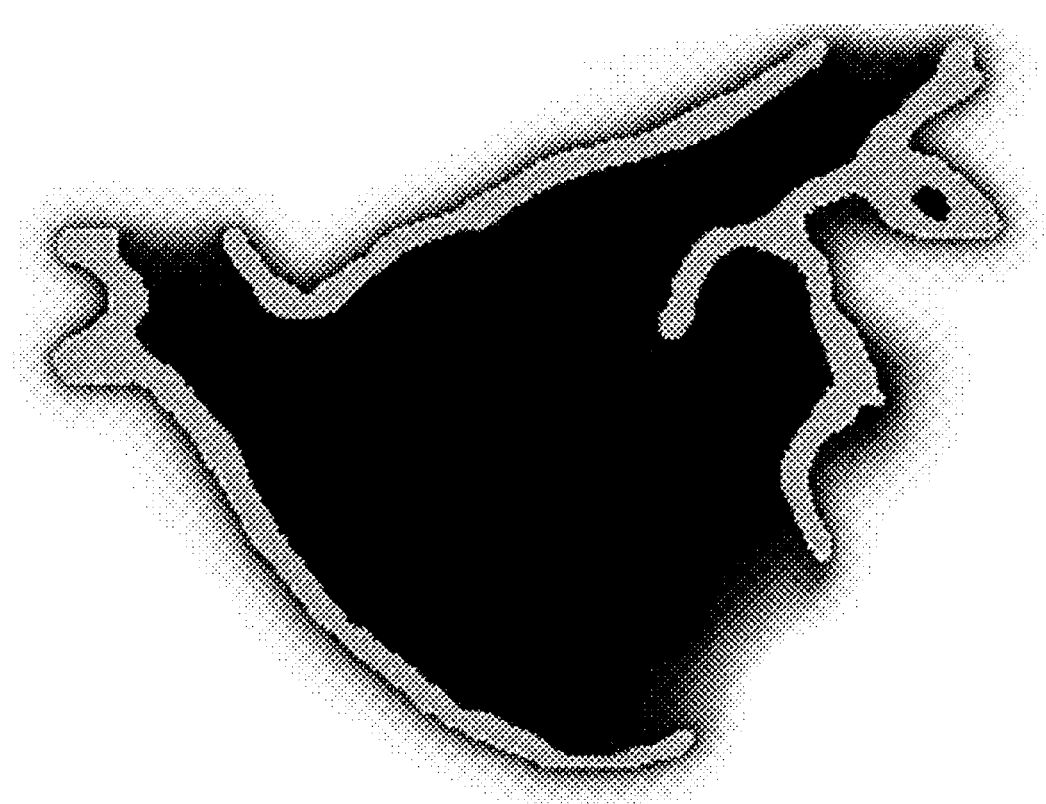
FIG. 12 is a diagram illustratively showing a result of repeatedly performing a Poisson equation 100 times on the two-dimensional atrial envelope shown in FIG. 11 using a Jacobian iteration method.

FIG. 12 is a diagram illustratively showing a result of repeatedly performing a Poisson equation 100 times on the two-dimensional atrial envelope shown in FIG. 11 using a Jacobian iteration method, wherein it can be seen that the atrial wall region is the same as before, an inner region of the atrium is displayed in a gradation toward the atrial wall region, and a region other than the atrial envelope is also displayed in a gradation toward the atrial wall region, and herein, the region displayed in the gradation is an inside of the atrial envelope, but corresponds to a region that can be regarded as an inner region of the atrium, within a region outside the atrial wall or an open region, and a three-dimensional atrial envelope is calculated above in step S220-1 in order to calculate a rate of change in the region.

In such a three-dimensional atrial envelope, a border of the atrial wall region and a border of a non-eroded region in the open region may be calculated by applying a cutoff frequency, and more specifically, by applying a cutoff frequency of 0.1, and a different cutoff frequency may of course be applied depending on the settings of the administrator or user of the device 100 including a processor and a memory.

Figure 13:
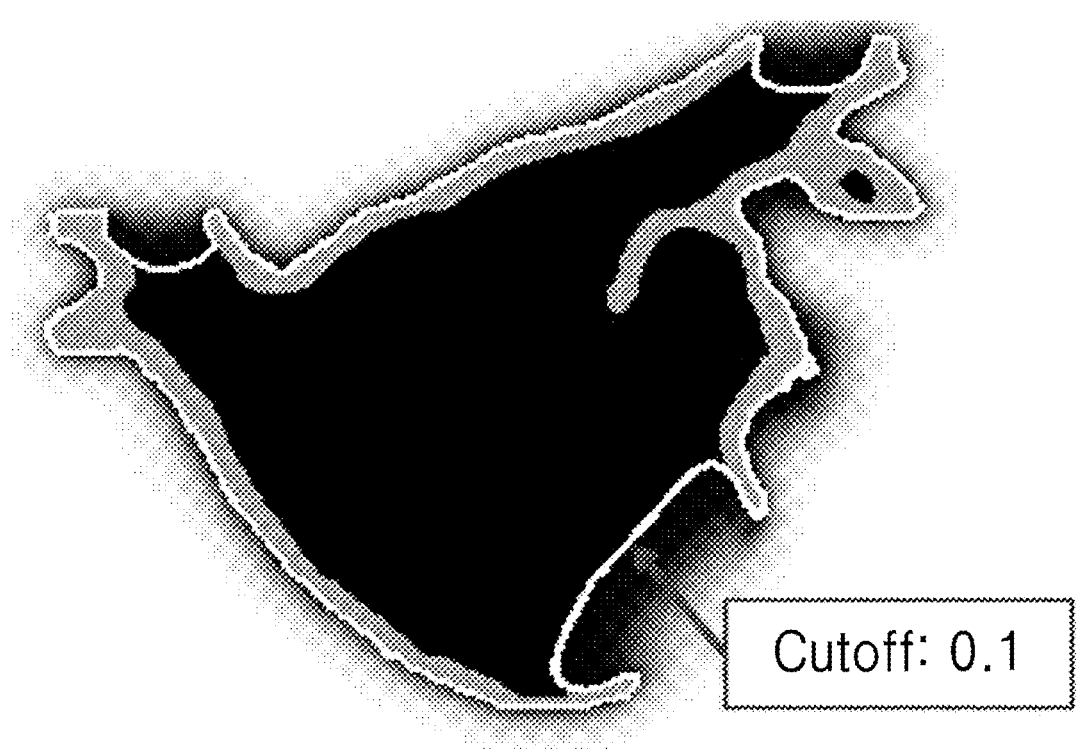
FIG. 13 is a diagram illustratively showing a result of applying a cutoff frequency of 0.1 to FIG. 12.

FIG. 13 is a diagram showing a result of applying the cutoff frequency of 0.1 to FIG. 12, wherein it can be seen that a border corresponding to the cutoff frequency of 0.1 is drawn along the epicardium, and the open region is also drawn with a border corresponding to the cutoff frequency of 0.1, and as a result, it can be seen that the region has been changed to a closed region.

In more detail, this cutoff frequency may be considered as a means of extracting a region that can be regarded as an atrial wall region and an inner region of the atrium included thereinside, which is meaningful because it can change an open region into a closed region, and an outer portion of the cutoff frequency displayed in the open region is displayed in a gradation, but should be regarded as an eroded region rather than the inner region of the atrium. Accordingly, the border of the non-eroded region in the open region calculated in step S220-3 may denote a border that can be regarded as an inner region of the atrium.

By applying the cutoff frequency, a border of the atrial wall region and a border of the non-eroded region in the open region may be calculated, and then the device 100 including a processor and a memory performs binarization on a region corresponding to the atrium and other regions based on the calculated borders of the atrial wall region and the non-eroded region in the open region (S220-4).

Figure 14:
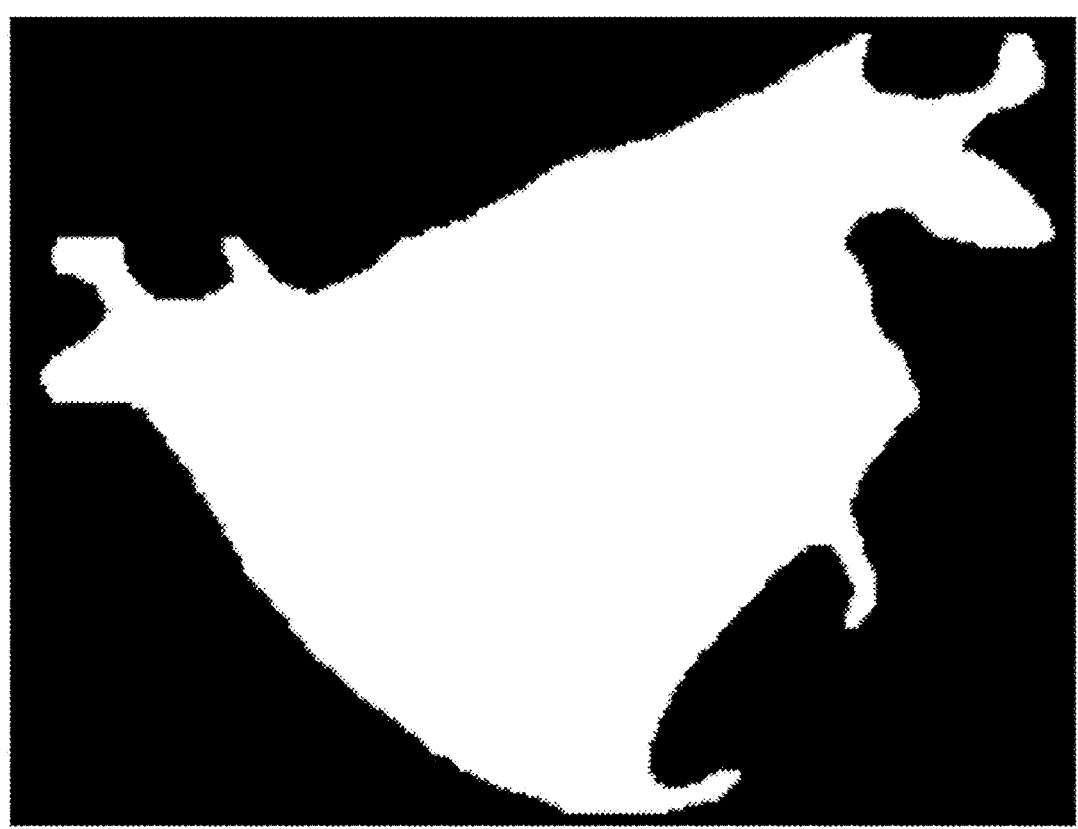
FIG. 14 is a diagram illustratively showing a result of performing binarization on FIG. 13.

Here, binarization is performed to easily distinguish between the region corresponding to the atrium, including an atrial wall region and an inner region of the atrium, and other regions, and FIG. 14 illustratively shows a result of performing binarization based on a border of the atrial wall region and a border of the non-eroded region in the open region as shown in FIG. 13.

According to steps S220-1 to S220-4 described above, an atrial wall region and a region corresponding the atrium including an inner region of the atrium, and borders thereof may be calculated, and for convenience of description, it has been described based on a diagram shown with a two-dimensional cross-section, but all steps may be regarded as being performed on a three-dimensional atrial envelope calculated in step S220-1, and accordingly, a resultant output in which step S220-4 has been performed may be regarded as a type of three-dimensional atrial model on which binarization has been performed based on a region corresponding to the atrium and a border thereof.

Meanwhile, even in a three-dimensional atrial model, some residues may remain outside the epicardium, and there is a need to remove these residues to more accurately calculate a region corresponding to the atrium. Accordingly, subsequent to step S220-4, residues may be removed using one or more pixels corresponding to a border of the region corresponding to the atrium and an atrial wall region on which binarization has been performed by the device 100 including a processor and a memory (S220-5).

In more detail, it is shown above in FIG. 13 that a border corresponding to the cutoff frequency of 0.1 is attached to the atrial wall region without any margin, but when the border is enlarged and examined in detail, there exist some margins, and thus the margins, which are regarded as residues, may be removed, thereby improving the accuracy of calculating the region corresponding to the atrium.

Figure 15:
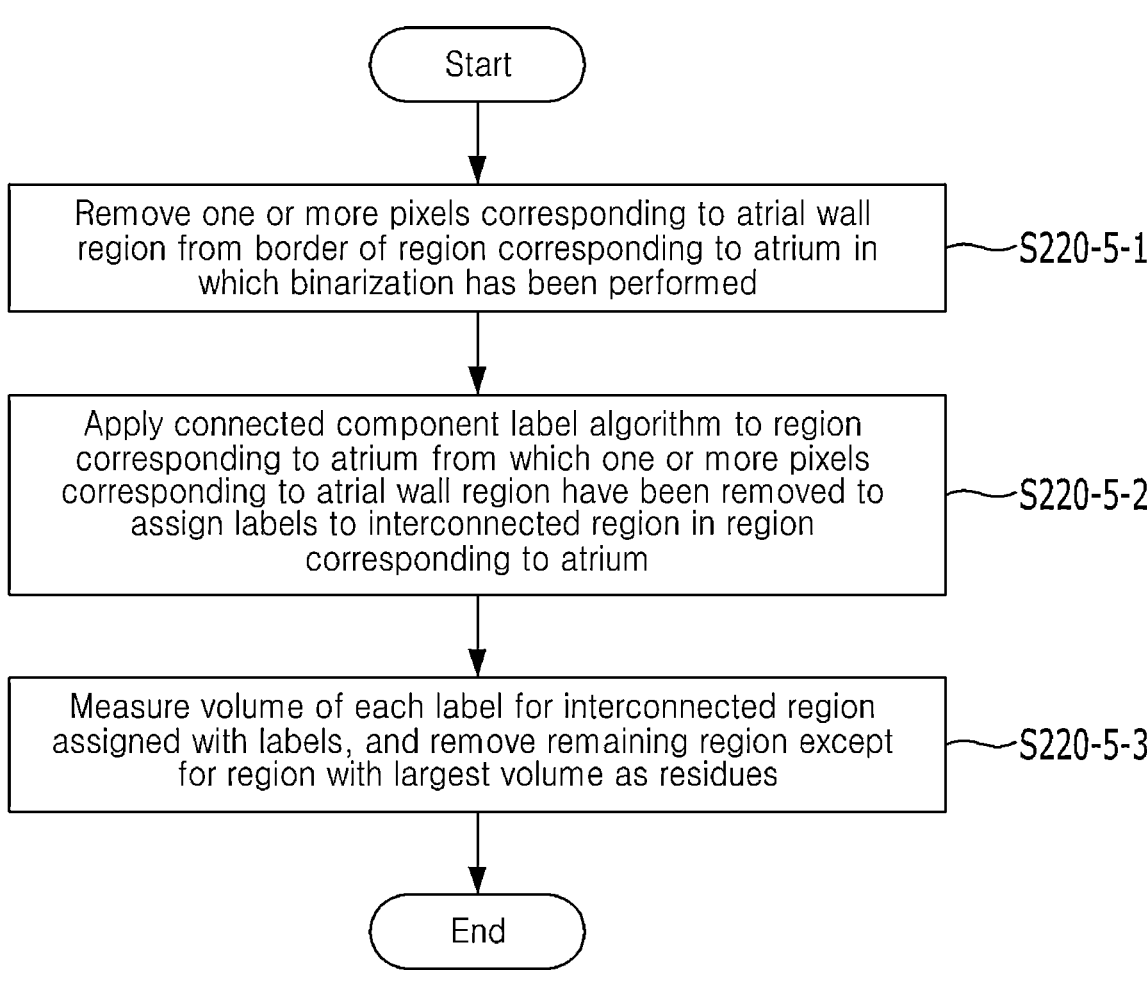
FIG. 15 is a flowchart illustrating a step S220-5 of removing residues.

Referring to FIG. 15, which is a flowchart of a specific method of removing residues, step S220-5 may include at least one of: removing one or more pixels corresponding to the atrial wall region from a border of the region corresponding to the atrium in which binarization has been performed by the device 100 including a processor and a memory (S220-5-1), applying a connected component label algorithm to a region corresponding to the atrium from which one or more pixels corresponding to the atrial wall region have been removed to assign labels to an interconnected region in the region corresponding to the atrium (S220-5-2), and measuring a volume of each label for the interconnected region assigned with the labels, and removing the remaining region except for a region with the largest volume as residues (S220-5-3).

Figure 16:
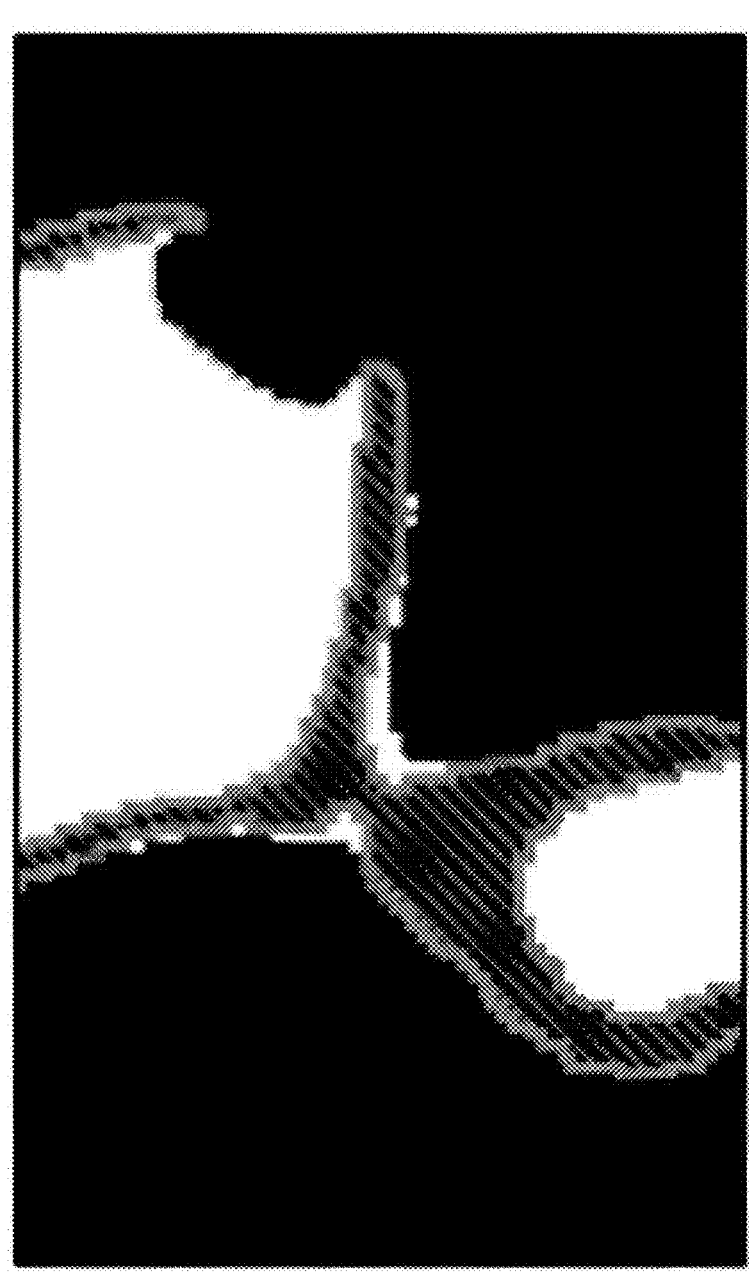
FIG. 16 is a diagram illustratively showing a region corresponding to the atrium on which binarization has been performed according to step S220-5-1, that is, a view in which pixels corresponding to an atrial wall region are removed from a cross-section of a three-dimensional atrial model.

For convenience of description, it will be described again based on a diagram showing a two-dimensional cross-section. FIG. 16 is a diagram illustratively showing a region corresponding to the atrium on which binarization has been performed according to step S220-5-1, that is, a view in which pixels corresponding to an atrial wall region are removed from a cross-section of a three-dimensional atrial model, wherein it can be seen that a finely white region is shown in upper and lower recessed portions in the middle of the diagram, which may be regarded as a region between a border of the region corresponding to the atrium and a border of the epicardium.

Figure 17:
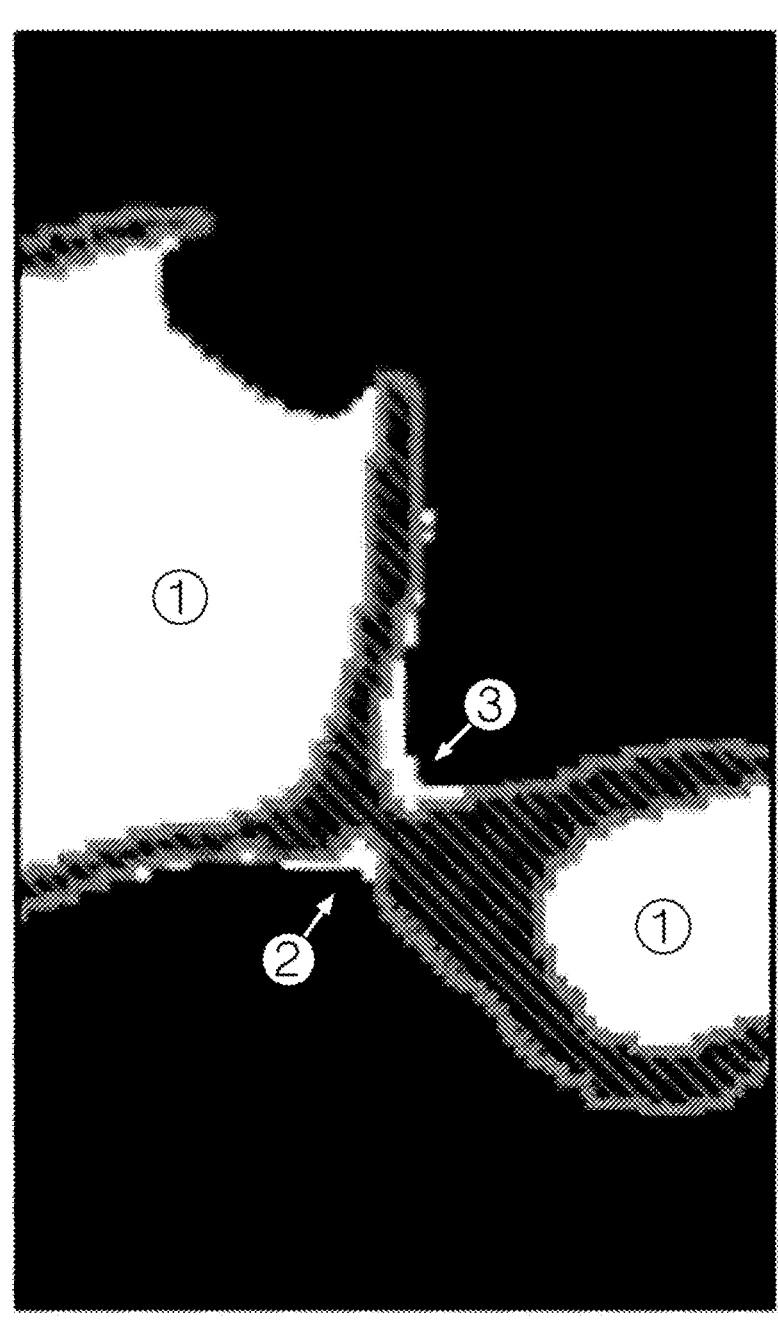
FIG. 17 is a diagram in which labels ①, ②, and ③ are assigned to respective regions by applying a connected component label algorithm to the regions shown in FIG. 16.

FIG. 17 for explaining step S220-5-2 is a diagram in which labels ①, ②, and ③ are assigned to respective regions by applying a connected component label algorithm to the regions shown in FIG. 16, wherein as described above, it is illustrated based on a two-dimensional cross-section for convenience of description, but steps S220-5-1 to S220-5-3 are performed on a three-dimensional atrial model, which is a region corresponding to the atrium in which binarization has been performed, and regions ①, ②, and ③, respectively, shown in FIG. 17, are assigned with labels because they are regions that can be three-dimensionally connected to a region shown in another two-dimensional cross-section of a three-dimensional atrium model.

Meanwhile, referring to FIG. 17, it can be seen that label ① is individually assigned to left and right sides based on labels ② and ③, which are recessed portions, which denotes that a region is divided into two portions by the atrial wall in the cross-section, but two regions are connected to each other so that they can be regarded as a single region through other cross-sections.

A volume of each label is measured for the regions connected to each other according to step S220-5-3, and by substituting the measured volume into FIG. 17, a region corresponding to ①, which is a region assigned with a label, may be measured to have the largest volume, and the remaining regions except for the region, assigned with label ② and label ③, are confirmed as residues and removed. This is because a region with the largest volume may be regarded as a region inside the atrium by reflecting a general view that an inside of the atrium is configured with one large region as a whole and is not divided into separate, independent regions, and a view in which the regions assigned with labels (and (shown in FIG. 17 are removed as residues is illustratively shown in FIG. 18.

When residues outside the atrial wall, more specifically, a region between a border of the region corresponding to the atrium and a border of the epicardium, has been removed, all preparations are completed to calculate endocardial and epicardial borders, and the description of FIG. 6 will be provided again.

Subsequent to removing the residues, a 3D connection filter is applied by the device 100 including a processor and a memory to each voxel corresponding to the atrial wall region including the region corresponding to the atrium to determine whether the voxel corresponds to any one region of the endocardium, myocardium, and epicardium, and label it to calculate endocardial and epicardial borders (S220-6).

Figure 18:
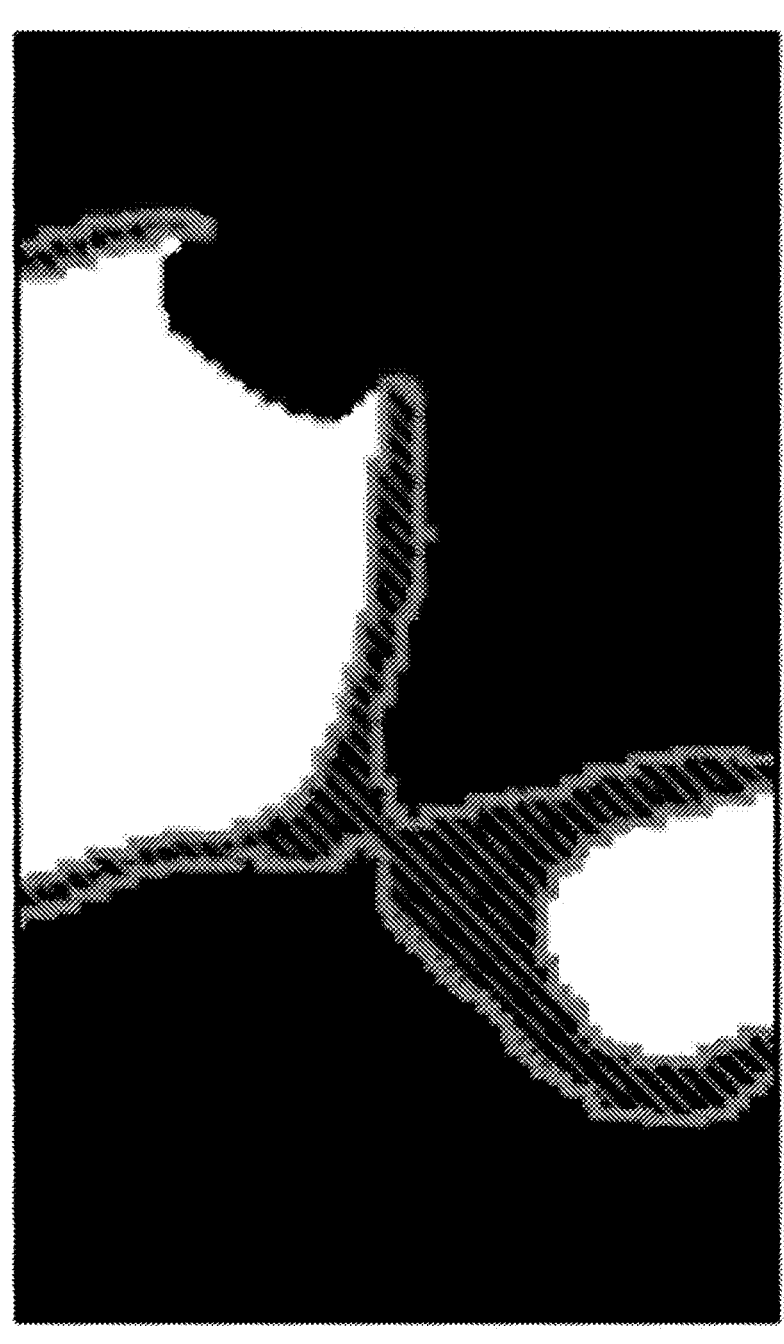
FIG. 18 is a diagram illustratively showing a view in which the regions assigned with labels ② and ③ shown in FIG. 17 are removed as residues.
Figure 19:
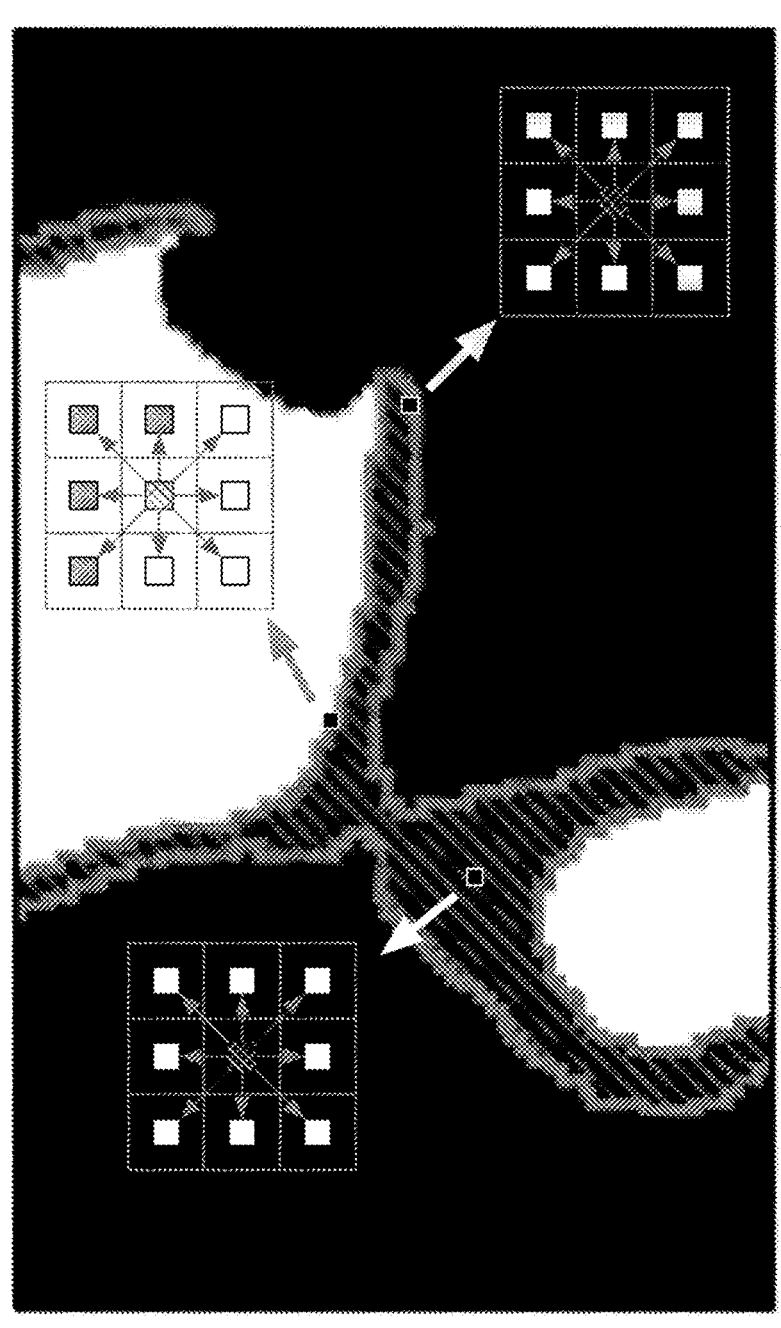
FIG. 19 is a diagram illustratively showing a result of applying a 3D connection filter to some pixels corresponding to an atrial wall region in the diagram shown in FIG. 18.

FIG. 19 is a diagram illustratively showing a result of applying a 3D connection filter to some pixels corresponding to an atrial wall region in the diagram shown in FIG. 18, wherein since the atrial wall region includes a plurality of pixels, checking which region eight pixels disposed adjacent to each pixel correspond to and labeling on the pixel is carried out.

More specifically, labeling may be carried out by determining a voxel as the epicardium when more than half of voxels adjacent thereto are voxels for a region other than the region corresponding to the atrium, the myocardium when more than half voxels adjacent thereto are voxels for the atrial wall region, and the endocardium when more than half of voxels adjacent thereto are voxels for a region having the largest volume, wherein referring to nine pixels in an upper right corner shown in FIG. 19, when named as pixel 1, pixel 2, and pixel 3, respectively, from the upper left to the right, pixel 4, the present pixel, and pixel 5 from the left in the next row, and pixel 6, pixel 7, and pixel 8 from the left in the next row, five pixels, which are pixels 1 to 3, pixel 5, and pixel 8, may be pixels corresponding to a region other than the region corresponding to the atrium, the present pixel may be labeled with a pixel corresponding to the epicardial region, and when named in a similar manner with reference to nine pixels in a lower left corner shown in FIG. 19, all pixels, which are pixel 1 to pixel 8, may be pixels corresponding to the atrial wall region, the present pixel may be labeled as a pixel corresponding to the atrial wall region.

In this case, in the case of the middle nine pixels shown in FIG. 19, four pixels, which are pixel 1, pixel 2, pixel 4, and pixel 6, are pixels corresponding to a region having the largest volume, and the remaining four pixels are pixels corresponding to the atrial wall region, and therefore, it may be problematic because either one is a half rather than a majority, but actual labeling is performed on three-dimensional voxels, not two-dimensional pixels, and since there are twenty six pixels disposed adjacent to one three-dimensional voxel, there will not be many cases where the number is calculated exactly in half, and even in such cases, a result corresponding to the majority of the labeling results for other voxels disposed adjacent thereto may be followed, and furthermore, it may be selected by the administrator or user of the device 100 including a processor and a memory.

Figure 20:
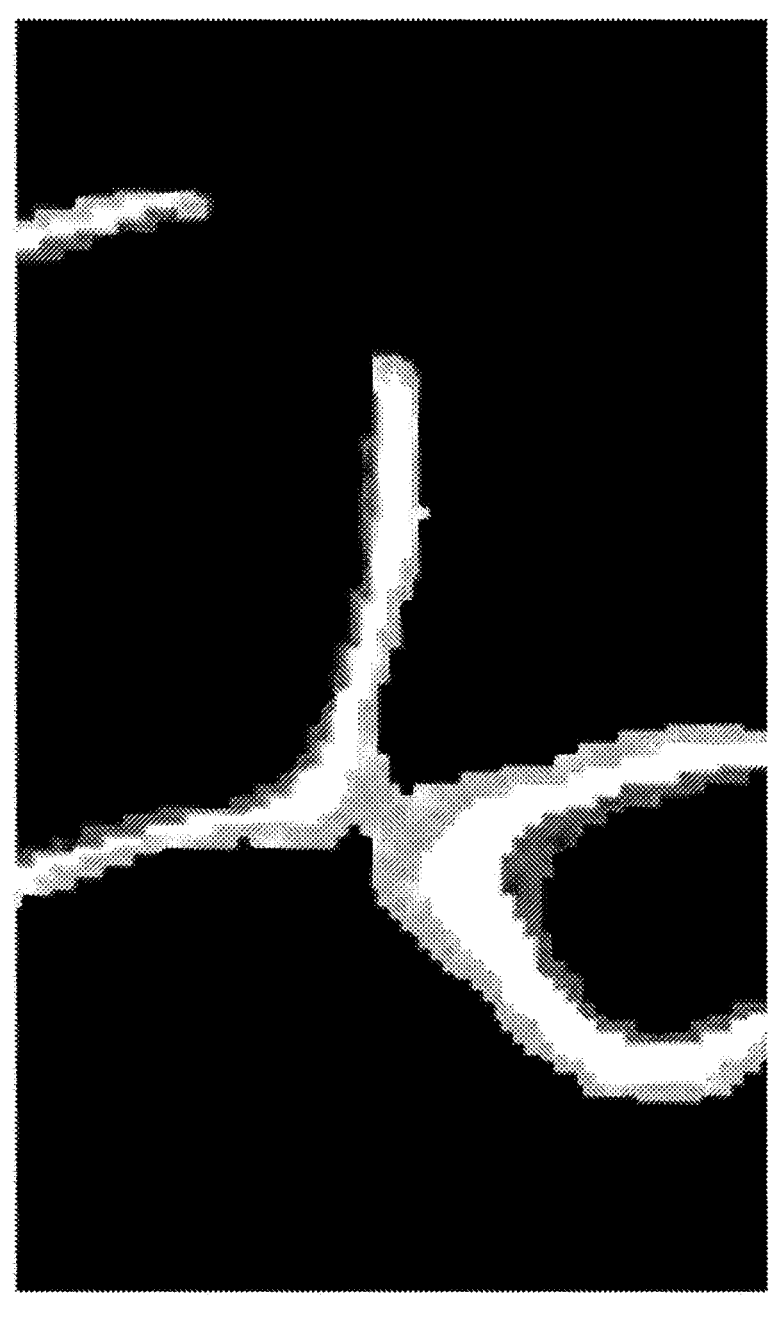
FIG. 20 is a diagram illustratively showing a result of calculating endocardial and epicardial borders by completing labeling for respective pixels corresponding to the atrial wall region shown in FIG. 19.

FIG. 20 is a diagram illustratively showing a result of calculating endocardial and epicardial borders by completing labeling for respective pixels corresponding to the atrial wall region shown in FIG. 19, wherein it can be seen that the respective pixels corresponding to the atrial wall region are shown in three colors, and from among them, a border including pixels in contact with a region having the largest volume is calculated as an endocardial border, and a border including pixels in contact with a region other than a region corresponding to the atrium as an epicardial bounder, and since both the endocardial and epicardial borders are calculated, the description of FIG. 2 will be provided again.

When endocardial and epicardial borders have been calculated, a patient's atrial wall thickness is finally calculated using the endocardial and epicardial borders calculated by the device 100 including a processor and a memory (S230).

A Laplace equation is used to finally calculate the patient's atrial wall thickness using the endocardial and epicardial borders, which will be described below with reference to FIG. 21.

FIG. 21 is a flowchart illustrating a step S230 of calculating an atrial wall thickness in the method of calculating the atrial wall thickness according to the second embodiment of the present disclosure.

This is only a preferred embodiment in achieving the objectives of the present disclosure, and some steps may be added thereto or deleted therefrom as needed, and furthermore, any one step may of course be included in another step.

First, 100 and 300 may be respectively set as initial conditions of a vector field for applying, by the device 100 including a processor and a memory, a Laplace equation to the calculated endocardial and epicardial borders (S230-1), and 200 may be set as an initial condition for a myocardial region between an endocardial border and an epicardial border.

Then, the device 100 including a processor and a memory performs the Laplace equation on any one voxel of a plurality of voxels adjacent to the endocardial border to calculate a gradient field representing a displacement of a part of an inside of the atrial wall region starting from the any one voxel (S230-2).

Here, the Laplace equation is as follows.

$$\nabla^2\Psi = \partial^2\Psi/\partial x^2 + \partial^2\Psi/\partial y^2 + \partial^2\Psi/\partial z^2$$

This Laplace equation may be performed through a Jacobian iteration method, and in this case, the Laplace equation may be expressed as follows.

$$\Psi_{i+1}(x,y,z) = \tfrac{1}{6}*[\Psi_i(x+\Delta x,y,z)+\Psi_i(x-\Delta x,y,z)+\Psi_i(x,y+\Delta y,z)+\Psi_i(x,y-\Delta y,z)+\Psi_i(x,y,z+\Delta z)+\Psi_i(x,y,z-\Delta z)]$$

In addition, the device 100 including a processor and a memory may also perform the following stopping condition equation once each time the Laplace equation is performed through the Jacobian iteration method.

Stopping condition equation $E_i = [(\Delta\Psi_i/\Delta x)^2 + (\Delta\Psi_i/\Delta y)^2 (\Delta\Psi_i/\Delta z)^2]^{1/2}$ More specifically, the device 100 including a processor and a memory performs the Laplace equation once and the stop condition expression once, and then determines each time whether the stopping condition $E_i$ corresponds to $10^{-5}$ or the number of repetitions of the Laplace equation corresponds to 400 or more, and performs, when it does not correspond thereto as a result of the determination, the Laplace equation again or also performs the stopping condition equation again to repeat a process of determining whether it corresponds thereto.

Here, the reason that the stopping condition $E_i$ is set to $10^{-5}$ or the number of repetitions of the Laplace equation is set to 400 or more is because in case where this stopping condition is satisfied, it may include, though starting from a voxel adjacent to the endocardial border, everything from the endocardial border to the epicardial border in a gradient field representing a displacement of a part of an inside of the atrial wall region. That is, the stopping condition may be a means of determining how far the gradient field will be calculated.

Figure 22:
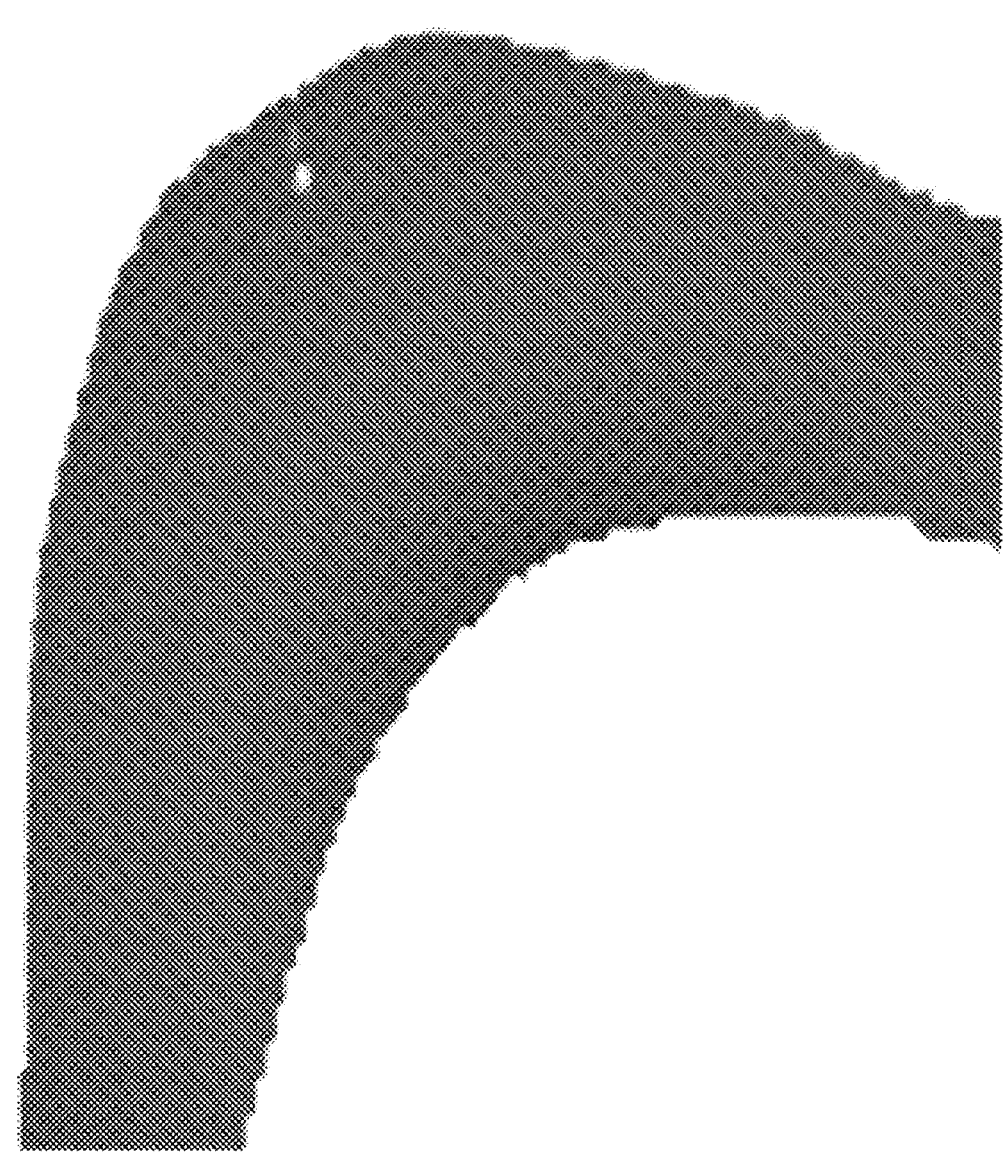
FIG. 22 is a diagram illustratively showing a gradient field of a region between an endocardial border and an epicardial border that is displayed in a gradation with different colors.

Then, the device 100 including a processor and a memory performs steps S230-1 and S230-2 on all of the plurality of voxels adjacent to the endocardial border to calculate a gradient field representing a displacement of an entire inside of the atrial wall region (S230-3), and a result thereof is illustratively shown in FIG. 22.

Referring to FIG. 22, it can be seen that a region between the endocardial border and the epicardial border is displayed in a gradation with different colors, wherein each color may be considered to represent a specific gradient.

When a gradient field representing the displacement of the entire inside of the atrial wall region is calculated, the device 100 including a processor and a memory applies an Euler method with $\Delta t$ set to 0.001 to any one voxel of a plurality of voxels adjacent to the endocardial border within the calculated gradient field representing the displacement of the entire inside of the atrial wall region to calculate a number of movements until an initial condition for the epicardial border is met (S230-4), multiplies the calculated number of movements by $\Delta t$ to calculate an atrial wall thickness in the any one voxel (S230-5), and performs steps S230-4 and S230-5 on all of the plurality of voxels adjacent to the endocardial border to calculate an atrial wall thickness in each voxel (S230-6).

Figure 23:
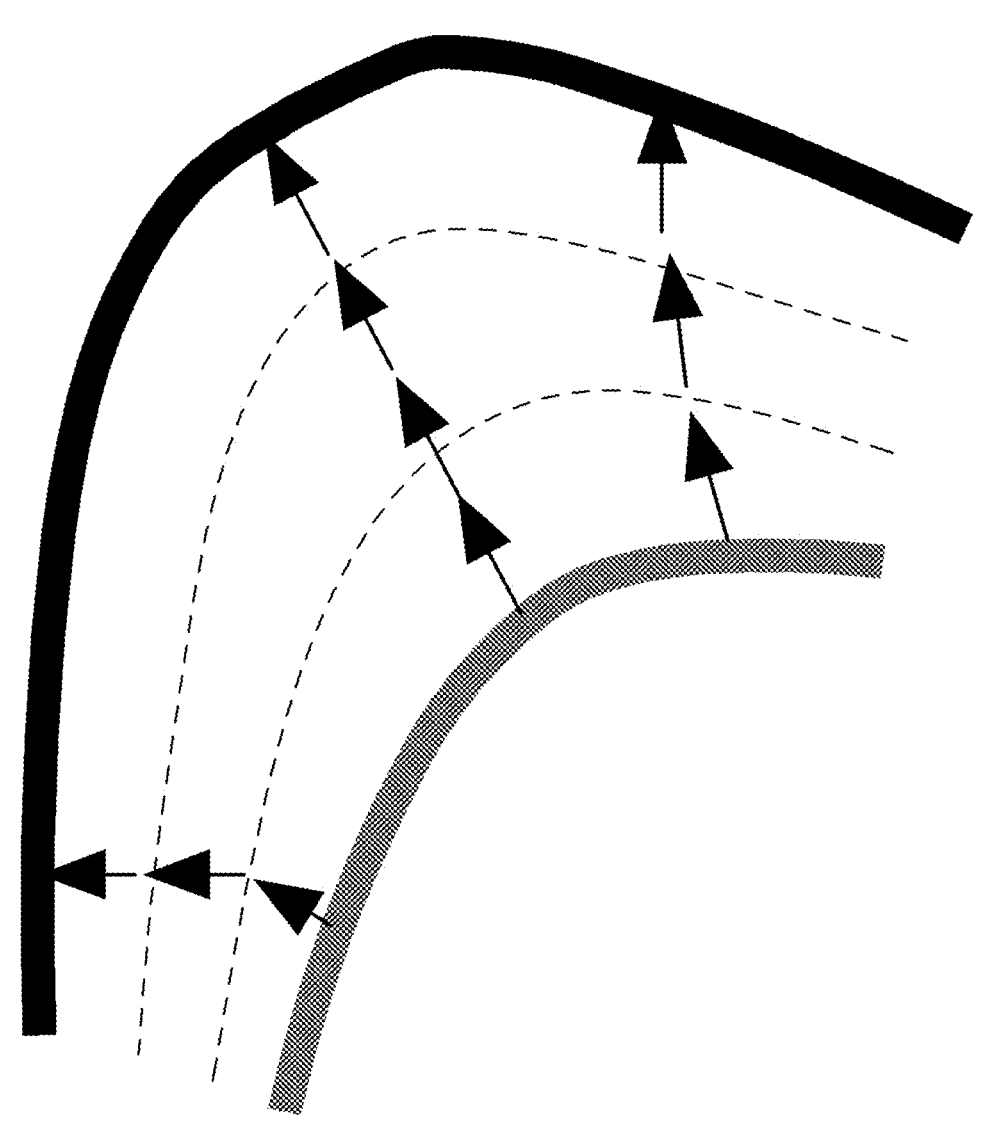
FIG. 23 is a diagram in which the number of movements, while from among a plurality of voxels adjacent to an endocardial border, any one voxel starts moving by $\Delta t$ along a gradient direction within a gradient field calculated at that voxel, and then repeatedly moves from the moved voxel again along the gradient direction within the gradient field at that voxel until it meets the epicardium, is illustratively shown by the number of arrows.
Figure 24:
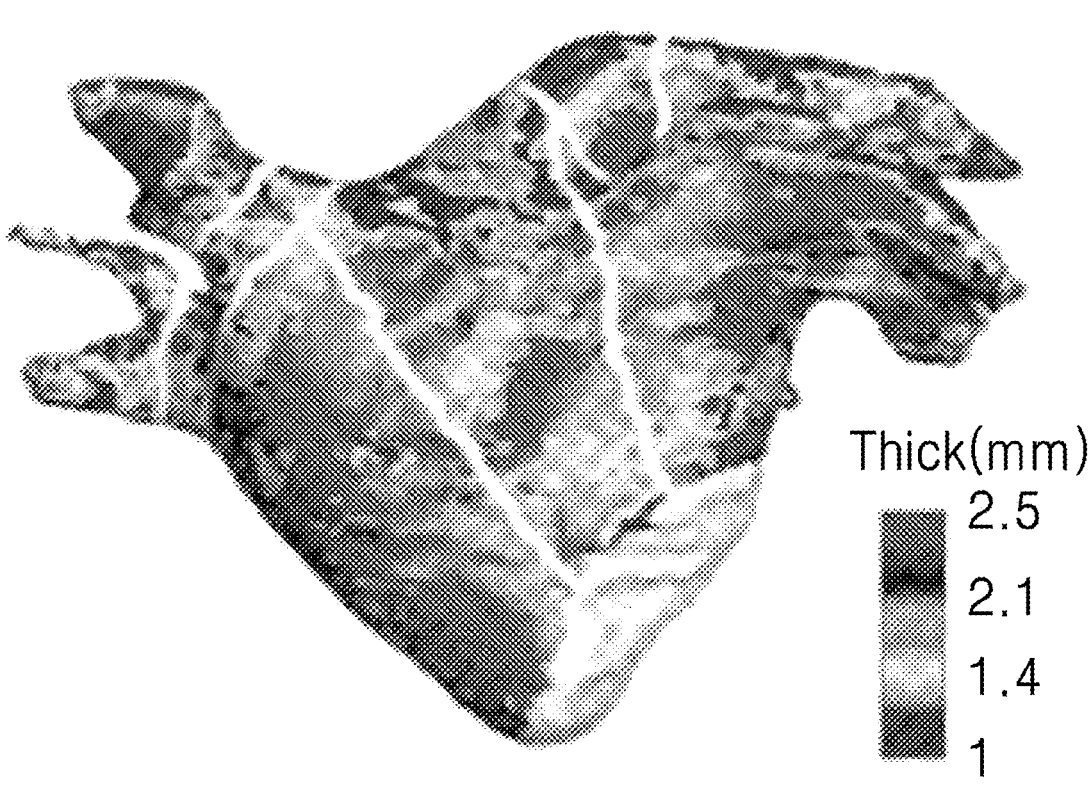
FIG. 24 is a diagram illustratively showing a view in which an atrial wall thickness is displayed in real time on a patient's three-dimensional atrium wall model.

This can be easily understood by referring to FIG. 23, wherein any one voxel of the plurality of voxels adjacent to the endocardial border starts moving by $\Delta t$ along a gradient direction within the gradient field previously calculated at that voxel, and repeatedly moves from the moved voxel again along the gradient direction within the gradient field at that voxel until it meets the epicardium to calculate the number of movements, and the number of movements is multiplied by $\Delta t$ corresponding to a movement distance per number of times to calculate an atrial wall thickness from the endocardial border to the epicardial border.

Describing this by substituting into FIG. 23, the bottom directional vectors shown in FIG. 23 have three arrows indicating the number of movements to move three times so as to encounter the epicardium, wherein 0.003 mm, which is 3*0.001, is a thickness of the atrial wall at that voxel, and the middle directional vectors have four arrows to move four times so as to encounter the epicardium, wherein an atrial wall thickness at that voxel is 0.004 mm, and the next vectors move three times, wherein 0.003 mm is calculated as a thickness of the atrial wall, and due to a limitation in showing the diagram, only three voxels are shown, but by performing this process on all voxels adjacent to the endocardium, a thickness of the atrial wall may be confirmed in an entire region corresponding to the atrium.

Up to the present, the method for calculating an atrial wall thickness according to the second embodiment of the present disclosure has been described. According to the present disclosure, mask label image data, which is input data used to calculate a patient's atrial wall thickness, may be generated by commercially available atrial wall automatic segmentation software to be received therefrom and thus may not be strongly coupled to a customized atrial wall segmentation technology as in the prior art, and as a result, may be easily applicable to and have high compatibility with commercially available atrial wall automatic segmentation software. Moreover, simply by receiving the input data, the patient's atrial wall thickness may be calculated fully automatically without receiving any input from the administrator or user of the device 100 including a processor and a memory, thereby acquiring consistent atrial wall thickness calculation results. Furthermore, when the processor 10 is implemented as the processor 10 capable of parallel processing, as illustratively shown in FIG. 24, the patient's atrial wall thickness may be calculated and output in real time, thereby facilitating the determination of a surgical intensity of a high-frequency electrode catheter ablation procedure.

Figure 25:
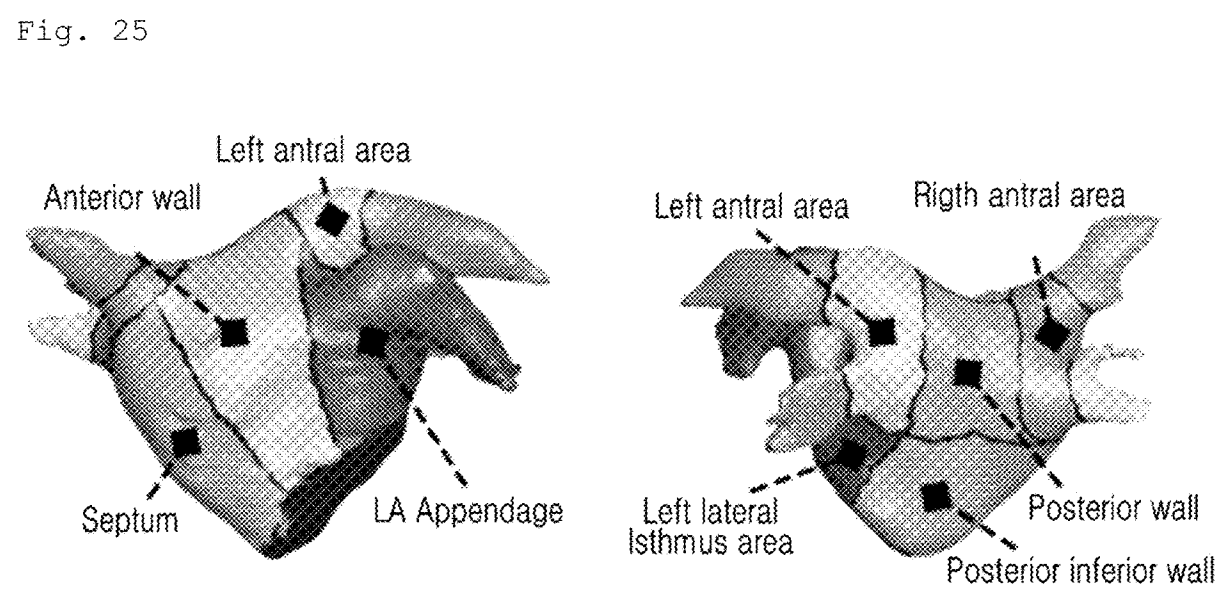
Figure 26:
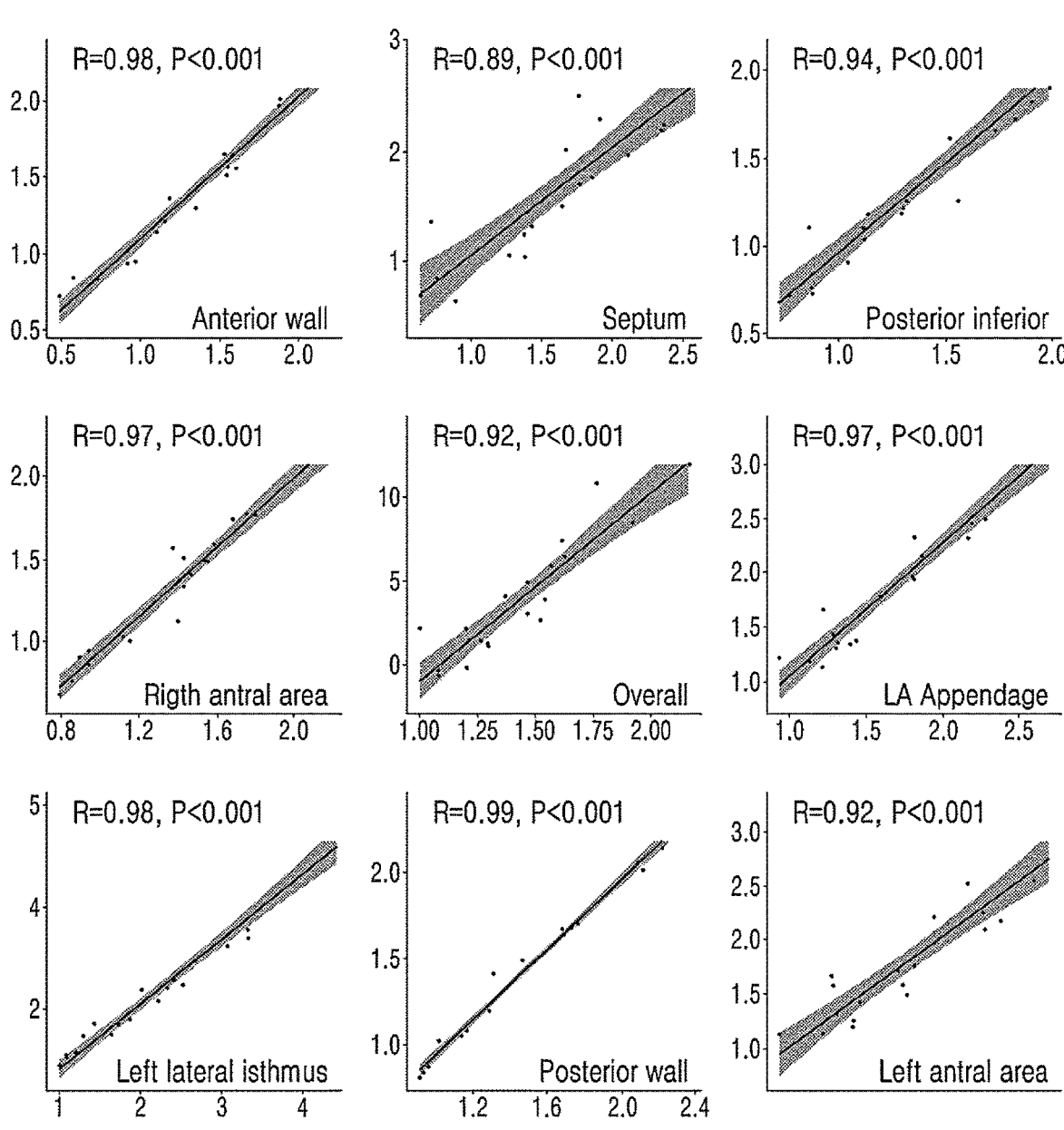
FIG. 26 is graphs showing correlations between left atrial wall thickness calculation results according to Publication No. 10-2020-0095967 for twenty patients and left atrial wall thickness calculation results based on an atrial wall thickness calculation device according to the second embodiment of the present disclosure.

FIG. 25 illustratively shows a view in which a patient's atrium is divided into zones, and FIG. 26 is graphs showing correlations between left atrial wall thickness calculation results according to Publication No. 10-2020-0095967 for twenty patients and left atrial wall thickness calculation results based on an atrial wall thickness calculation device according to the second embodiment of the present disclosure.

According to the Korean Publication No. 10-2020-0095967, an average left atrial wall thickness was 1.43±0.29 mm, and according to the atrial wall thickness calculation device according to the second embodiment of the present disclosure, it was 1.39±0.35 mm, and thus a correlation R between the two technologies was found to be very high at 0.918, and referring to FIG. 26, which shows the correlation between the results of calculating the atrial wall thickness by region of the atrium, it can be seen that the correlation R of the two technologies was between 0.89 and 0.99, showing very high accuracy. That is, according to the atrial wall thickness calculation device according to the second embodiment of the present disclosure, an atrial wall thickness may be calculated with similar high accuracy even in the absence of intervention by a highly skilled clinician.

Furthermore, time periods required to calculate the atrial wall thickness in the two technologies were measured, and it was confirmed that about 20 minutes was required according to the Korean Publication No. 10-2020-0095967, and about 30 seconds was required according to the atrial wall thickness calculation device according to the second embodiment of the present disclosure, and thus it was confirmed that the calculation speed was improved by about 40 times.

Meanwhile, although not described in detail to prevent redundant description, the device 100 of calculating an atrial wall thickness according to the first embodiment of the present disclosure and the method for calculating an atrial wall thickness according to the second embodiment of the present disclosure may be implemented with a computer program stored in a medium according to the third embodiment of the present disclosure including the same technical features. In this case, a computer program stored on a medium may include (AA) receiving, in connection with a computing device, image data for the patient's atrium as input data, (BB) calculating endocardial and epicardial borders corresponding to starting and ending points of the atrial wall thickness from the received input data, and (CC) calculating the patient's atrial wall thickness using the calculated boundaries of the endocardium and epicardium, wherein the image data for the patient's atrium received in the step (AA) is a plurality of mask label image data for respective tomographic images of the patient's atrium acquired from computed tomography (CT) scans for the patient's atrium, and the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions, and the device 100 of calculating an atrial wall thickness according to the first embodiment of the present disclosure and the method for calculating an atrial wall thickness according to the second embodiment of the present disclosure may produce the same effect.

As described above, the embodiments of the present disclosure have been described with reference to the accompanying drawings, but it will be apparent to those skilled in the art to which the invention pertains that the invention can be embodied in other specific forms without departing from the concept and essential characteristics thereof. Therefore, it should be understood that the foregoing embodiments are merely illustrative but not restrictive in all aspects.

The invention claimed is:

1. A method of calculating an atrial wall thickness through a device including a processor and a memory, the method comprising:

(a) receiving image data for a patient's atrium as input data;

(b) calculating endocardial and epicardial borders corresponding to starting and ending points of the atrial wall thickness from the received input data; and (c) calculating the patient's atrial wall thickness using the calculated endocardial and epicardial borders, wherein the image data for the patient's atrium received in the step (a) is a plurality of mask label image data for respective tomographic images of the patient's atrium acquired from computed tomography (CT) scans for the patient's atrium, wherein the mask label image data is data in which one or more pixels corresponding to an atrial wall region including the patient's atrium and an inner region of the atrium, other regions within the patient's heart disposed around the patient's atrium, and regions other than the patient's heart, respectively, are assigned with labels having different numerals for the respective regions, and wherein the step (b) comprises at least one of:

(b-1) extracting one or more pixels corresponding to an atrial wall region from the received input data, and applying a convex hull algorithm thereto to calculate a three-dimensional atrial envelope for the patient's atrium;

(b-2) setting an initial boundary condition for performing a Poisson equation on the calculated three-dimensional atrial envelope;

(b-3) repeatedly performing the Poisson equation N times (N is a natural number) on the three-dimensional atrial envelope, and calculating a border of an atrial wall region in the three-dimensional atrial envelope and a border of a non-eroded region in an open region; and (b-4) performing binarization for a region corresponding to the atrium and a region other than the atrium based on the calculated borders of the atrial wall region and the non-eroded region in the open region.

2. The method of claim 1, wherein the step (b-1) comprises at least one of:

(b-1-1) extracting one or more pixels for the atrial wall region from any one of a plurality of mask label image data for each tomography image of the patient's atrium, which is the received input data;

(b-1-2) calculating a two-dimensional atrial envelope including an entire atrial wall region from which the one or more pixels are extracted thereinside by applying a convex hull algorithm thereto;

(b-1-3) performing the steps (b-1-1) and (b-1-2) for all of the plurality of mask label image data to calculate a plurality of two-dimensional atrial envelopes corresponding to the plurality of mask label image data, respectively; and (b-1-4) merging the calculated plurality of two-dimensional atrial envelopes to calculate a three-dimensional atrial envelope for the patient's atrium.

3. The method of claim 1, wherein the initial boundary condition set in the step (b-2) is a Neumann boundary condition for the atrial wall region included in the calculated three-dimensional atrial envelope, and a Dirichlet boundary condition for a region other than the calculated three-dimensional atrial envelope.

4. The method of claim 1, wherein the Poisson equation performed in the step (b-3) is performed through a Jacobi iteration method, and in this case, the number N is 100.

5. The method of claim 1, wherein a border of the atrial wall region and a border of the non-eroded region in the open region, which are included in the three-dimensional atrial envelope, are calculated by applying a cutoff frequency of 0.1 thereto.

6. The method of claim 1, further comprising:

subsequent to the step (b-4), (b-5) removing residues using a border of the region corresponding to the atrium in which binarization has been performed and one or more pixels corresponding to the atrial wall region.

7. The method of claim 6, wherein the step (b-5) comprises at least one of:

(b-5-1) removing one or more pixels corresponding to the extracted atrial wall region from the border of the region corresponding to the atrium in which binarization has been performed;

(b-5-2) applying a connected component label algorithm to a region corresponding to the atrium from which one or more pixels corresponding to the atrial wall region have been removed to assign labels to an interconnected region in the region corresponding to the atrium; and (b-5-3) measuring a volume of each label for the interconnected region assigned with the labels, and removing the remaining region except for a region with the largest volume as residues.

8. The method of claim 7, further comprising:

subsequent to the step (b-5), (b-6) applying a 3D connection filter to each voxel corresponding to the atrial wall region including the region corresponding to the atrium to determine whether the voxel corresponds to any one region of the endocardium, myocardium, and epicardium, and labeling it to calculate endocardial and epicardial borders.

9. The method of claim 8, wherein as a result of applying a 3D connection filter to each voxel, the region is determined as the epicardium when more than half of voxels adjacent thereto are voxels for a region other than the region corresponding to the atrium, as the myocardium when more than half of voxels adjacent thereto are voxels for the atrial wall region, and as the endocardium when more than half of voxels adjacent thereto are voxels for a region having the largest volume.

10. The method of claim 1, wherein the step (c) comprises at least one of:

(c-1) setting 100 and 300 as initial conditions of a vector field for applying a Laplace equation to the calculated endocardial and epicardial borders, respectively;

(c-2) performing the Laplace equation on any one voxel of a plurality of voxels adjacent to the endocardial border to calculate a gradient field representing a displacement of a part of an inside of the atrial wall region starting from the any one voxel;

(c-3) performing the steps (c-1) and (c-2) on all of the plurality of voxels adjacent to the endocardial border to calculate a gradient field representing a displacement of an entire inside of the atrial wall region;

(c-4) applying an Euler method with $\Delta t$ set to 0.001 to any one voxel of a plurality of voxels adjacent to the endocardial border within the calculated gradient field representing the displacement of the entire inside of the atrial wall region to calculate a number of movements until an initial condition for the epicardial border is met;

(c-5) multiplying the calculated number of movements by $\Delta t$ to calculate an atrial wall thickness in the any one voxel; and (c-6) performing the steps (c-4) and (c-5) on all of the plurality of voxels adjacent to the endocardial border to calculate an atrial wall thickness in each voxel.

11. The method of claim 10, wherein the Laplace equation performed in the step (c-2) is performed through a Jacobi iteration method, and wherein as for a stopping condition, a stopping condition equation, E is $10^{-5}$, or a number of repetitions is 400 or more, wherein the stopping condition equation is: $E_i = \Sigma [(\Delta \Psi_i / \Delta x)^2 + (\Delta \Psi_i / \Delta y)^2 (\Delta \Psi_i / \Delta z)^2]^{1/2}$.

12. A device of calculating an atrial wall thickness, the device comprising:

one or more processors;

a network interface;

a memory that loads a computer program executed by the processor; and a storage that stores large-capacity network data and the computer program, wherein the computer program comprises, by the one or more processors, (A) an operation of receiving image data for a patient's atrium as input data;

(B) an operation of calculating endocardial and epicardial borders corresponding to starting and ending points of the atrial wall thickness from the received input data; and (C) an operation of calculating the patient's atrial wall thickness using the calculated boundaries of the endocardium and epicardium, wherein the image data for the patient's atrium received in the operation (A) is a plurality of mask label image data for respective tomographic images of the patient's atrium acquired from computed tomography (CT) scans for the patient's atrium, wherein the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions, and wherein the operation (B) comprises at least one of:

(B-1) extracting one or more pixels corresponding to an atrial wall region from the received input data, and applying a convex hull algorithm thereto to calculate a three-dimensional atrial envelope for the patient's atrium;

(B-2) setting an initial boundary condition for performing a Poisson equation on the calculated three-dimensional atrial envelope;

(B-3) repeatedly performing the Poisson equation N times (N is a natural number) on the three-dimensional atrial envelope, and calculating a border of an atrial wall region in the three-dimensional atrial envelope and a border of a non-eroded region in an open region; and (B-4) performing binarization for a region corresponding to the atrium and a region other than the atrium based on the calculated borders of the atrial wall region and the non-eroded region in the open region.

13. A non-transitory computer-readable medium storing a computer program, the computer program comprising:

(AA) receiving, in connection with a computing device, image data for the patient's atrium as input data;

(BB) calculating endocardial and epicardial borders corresponding to starting and ending points of the atrial wall thickness from the received input data; and (CC) calculating the patient's atrial wall thickness using the calculated boundaries of the endocardium and epicardium, wherein the image data for the patient's atrium received in the step (AA) is a plurality of mask label image data for respective tomographic images of the patient's atrium acquired from computed tomography (CT) scans for the patient's atrium, wherein the mask label image data is data in which one or more pixels corresponding to an atrial wall region including the patient's atrium and an inner region of the atrium, other regions within the patient's heart disposed around the patient's atrium, and regions other than the patient's heart, respectively, are labeled with different numerals for the respective regions, and wherein the step (BB) comprises at least one of:

(BB-1) extracting one or more pixels corresponding to an atrial wall region from the received input data, and applying a convex hull algorithm thereto to calculate a three-dimensional atrial envelope for the patient's atrium;

(BB-2) setting an initial boundary condition for performing a Poisson equation on the calculated three-dimensional atrial envelope;

(BB-3) repeatedly performing the Poisson equation N times (N is a natural number) on the three-dimensional atrial envelope, and calculating a border of an atrial wall region in the three-dimensional atrial envelope and a border of a non-eroded region in an open region; and (BB-4) performing binarization for a region corresponding to the atrium and a region other than the atrium based on the calculated borders of the atrial wall region and the non-eroded region in the open region.

* * * * *